(12) United States Patent
Brodnick et al.

(10) Patent No.: US 11,113,814 B2
(45) Date of Patent: *Sep. 7, 2021

(54) DETERMINING RESPIRATORY PHASE FROM FLUOROSCOPIC IMAGES

(71) Applicant: APN Health, LLC, Pewaukee, WI (US)

(72) Inventors: Donald Brodnick, Cedarburg, WI (US); Shivani Kohut, Fayetteville, NC (US)

(73) Assignee: APN Health, LLC, Pewaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/693,021

(22) Filed: Nov. 22, 2019

(65) Prior Publication Data

US 2020/0090336 A1 Mar. 19, 2020

Related U.S. Application Data

(63) Continuation-in-part of application No. 15/891,669, filed on Feb. 8, 2018, now Pat. No. 10,489,911.

(51) Int. Cl.
*G06T 7/00* (2017.01)
*G06T 5/20* (2006.01)
*A61B 6/00* (2006.01)

(52) U.S. Cl.
CPC ............ *G06T 7/0016* (2013.01); *A61B 6/485* (2013.01); *A61B 6/5217* (2013.01); *G06T 5/20* (2013.01); *G06T 2207/10064* (2013.01); *G06T 2207/20021* (2013.01)

(58) Field of Classification Search
CPC .......... A61B 8/06; G06K 2009/00939; G06K 9/00221; G06T 7/0012
See application file for complete search history.

(56) References Cited

U.S. PATENT DOCUMENTS

| | | | | |
|---|---|---|---|---|
| 7,774,052 B2* | 8/2010 | Burton | ................ | A61B 5/4809 600/544 |
| 7,953,204 B2* | 5/2011 | Sumanaweera | ...... | A61N 5/1049 378/65 |
| 8,554,307 B2* | 10/2013 | Razzaque | .............. | A61B 5/748 600/424 |

(Continued)

*Primary Examiner* — Yosef Kassa
(74) *Attorney, Agent, or Firm* — Jansson Munger McKinley & Kirby Ltd.

(57) ABSTRACT

A method of determining respiratory phase of a living body from a sequence of digitized fluoroscopic images of a living-body region exhibiting respiratory displacement, the method employing programmable computing apparatus and comprising the steps of: (a) in each living-body-region image in the sequence, defining one or more zones with each image having identical image-to-image zone locations, sizes, and shapes; (b) for each image, computing an average pixel intensity for each zone to form a sequence thereof for each zone; (c) for each zone, modifying the average pixel intensities by (i) computing the mean value of the sequence of average pixel intensities for such zone, and (ii) subtracting the mean from each average pixel intensity in the zone; (d) for each zone sequence, computing a figure-of-merit; (e) selecting the zone having the highest figure-of-merit; and (f) using the sequence of pixel intensities of the selected zone to determine respiratory phase.

9 Claims, 21 Drawing Sheets

(56) References Cited

U.S. PATENT DOCUMENTS

| | | | |
|---|---|---|---|
| 8,781,197 B2 * | 7/2014 | Wang ................... | G01R 33/563 |
| | | | 382/131 |
| 8,849,388 B2 | 9/2014 | Brodnick et al. | |
| 9,076,201 B1 * | 7/2015 | Negahdar ................. | G06T 7/30 |
| 9,393,445 B2 | 7/2016 | Yamada et al. | |
| 10,646,183 B2 | 4/2020 | Ben-Haim | |

* cited by examiner

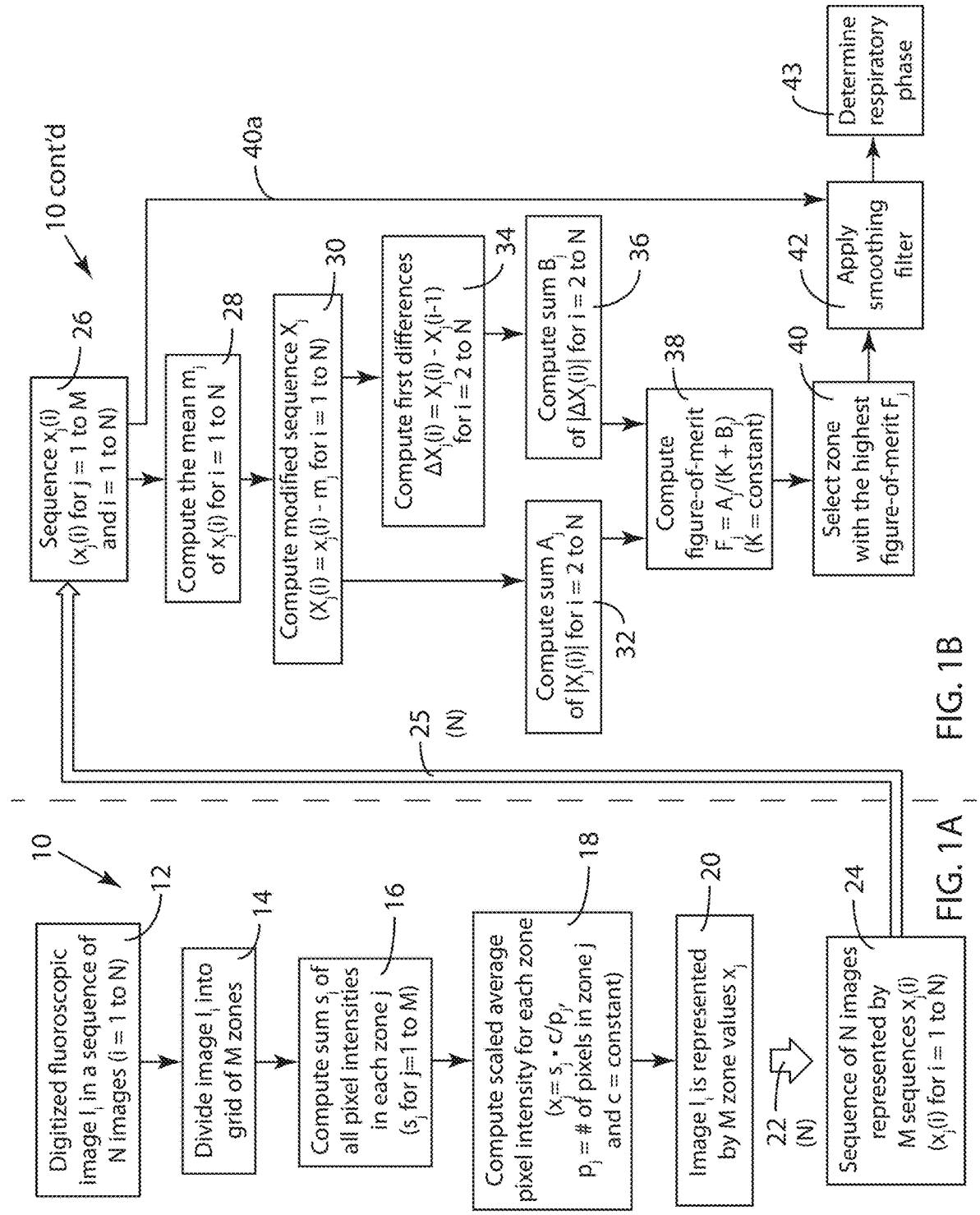
FIG. 1A | FIG. 1B

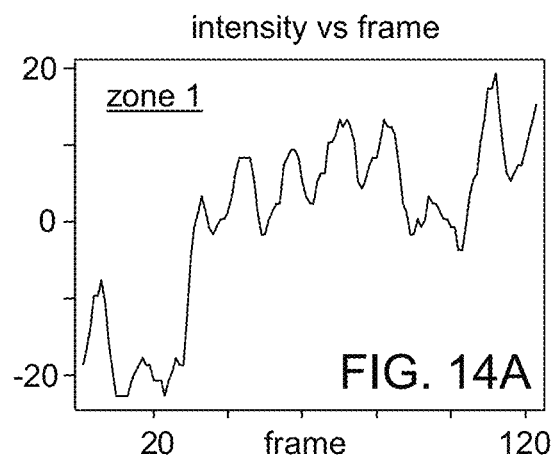
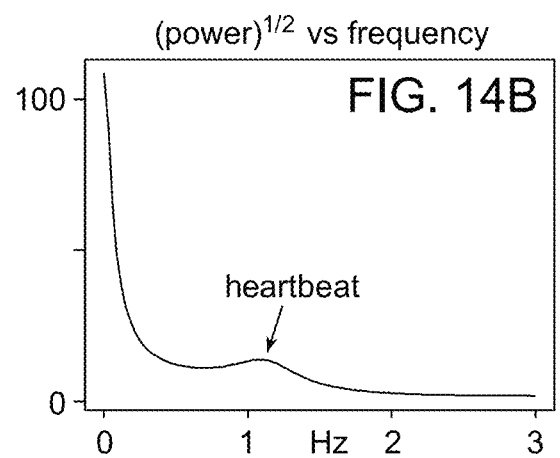
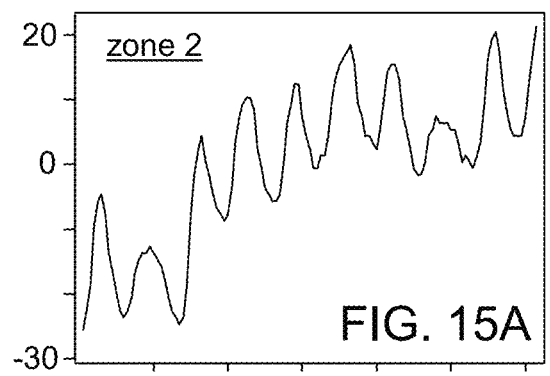
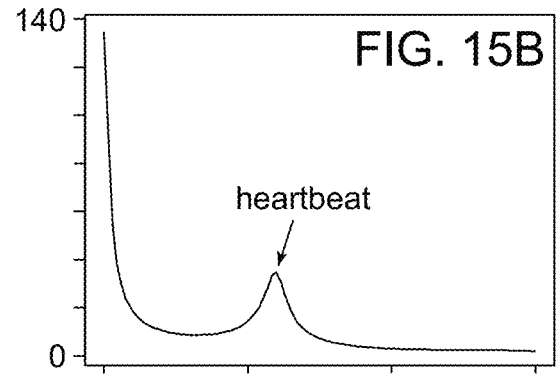
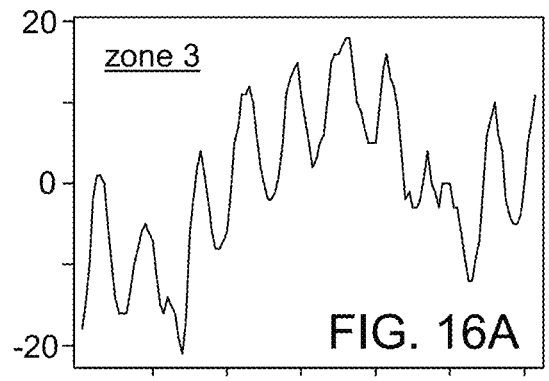
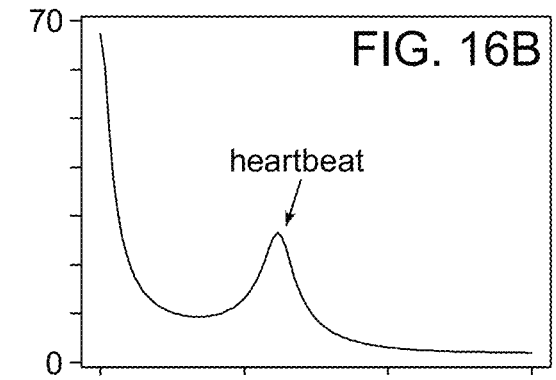
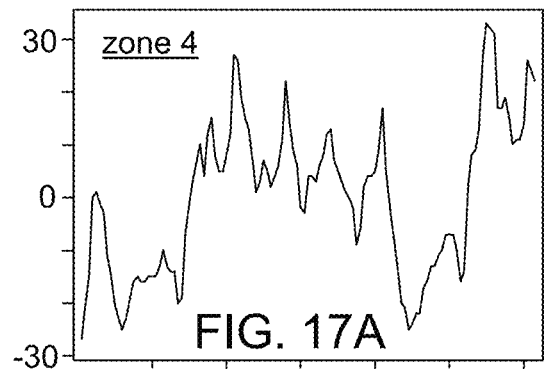
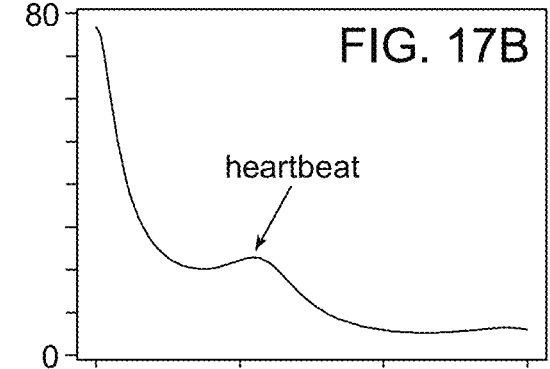

intensity vs frame        (power)$^{1/2}$ vs frequency
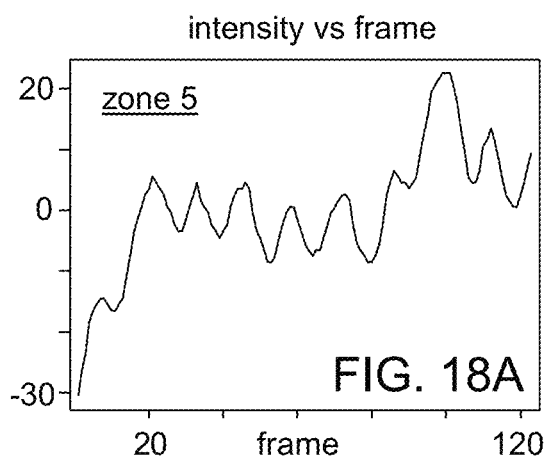
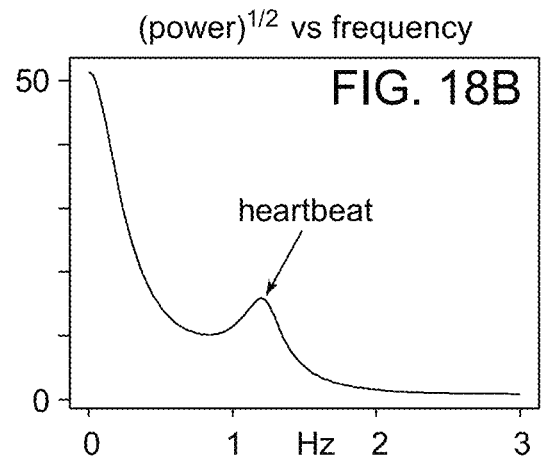
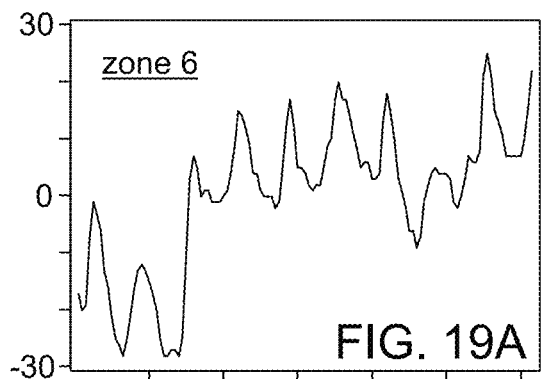
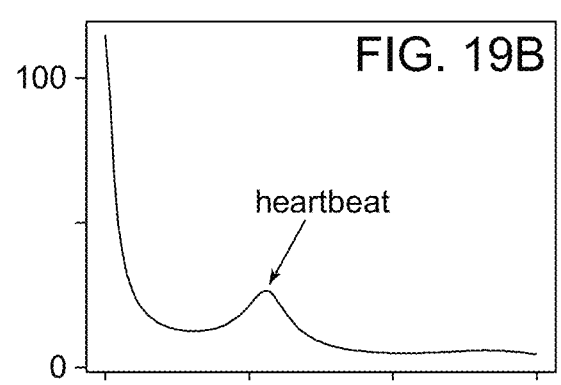
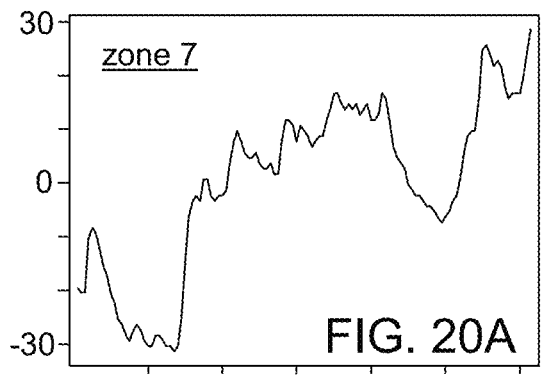
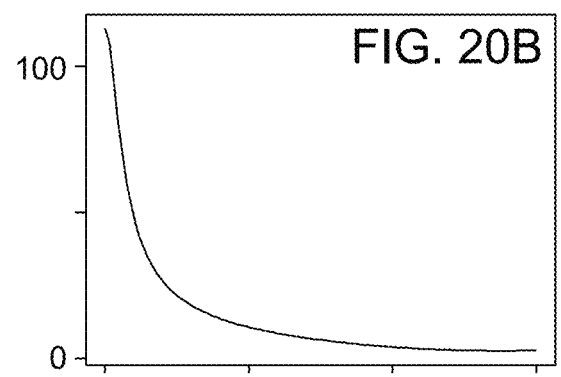
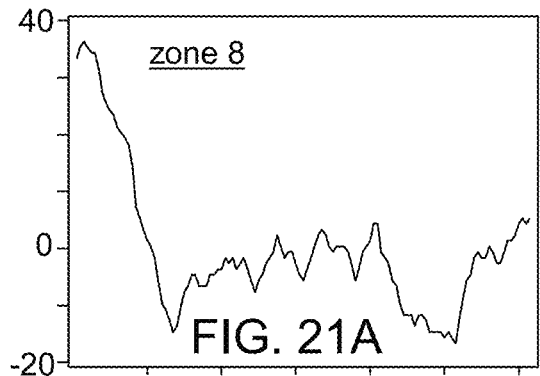
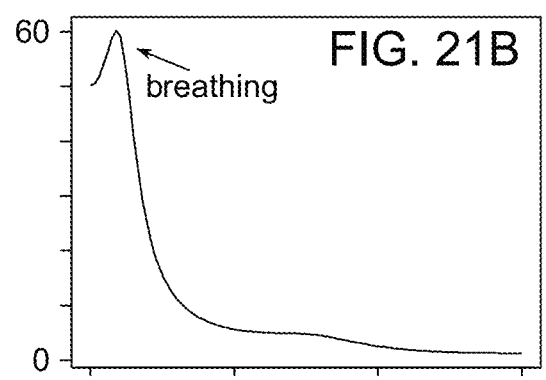

intensity vs frame (power)^{1/2} vs frequency

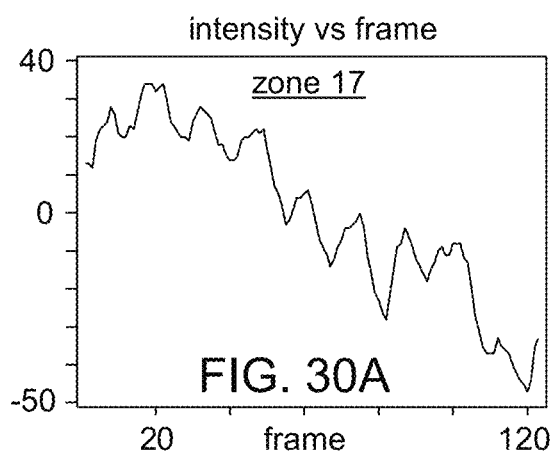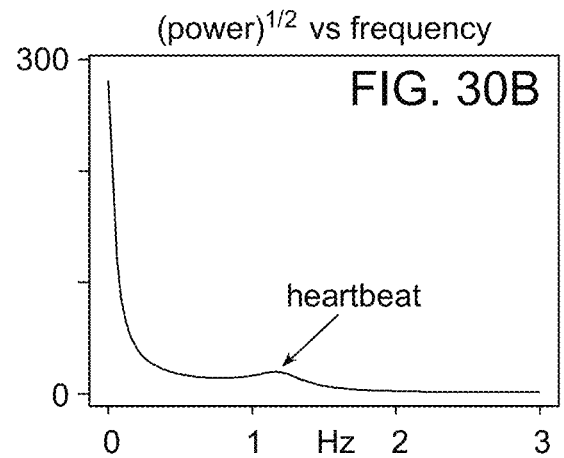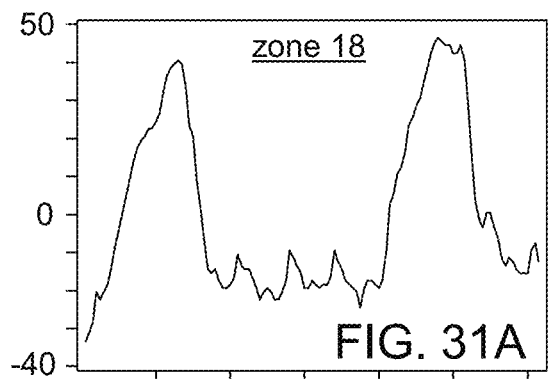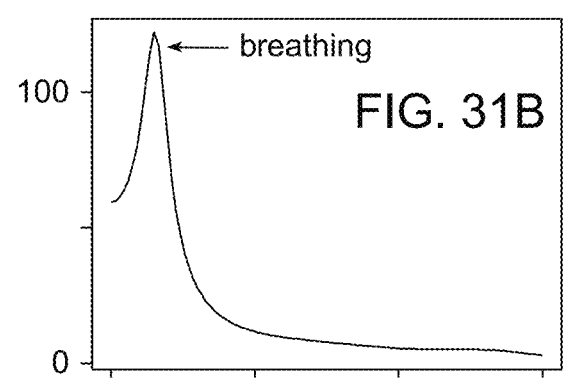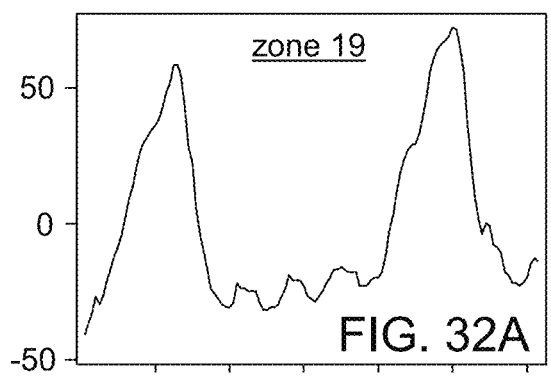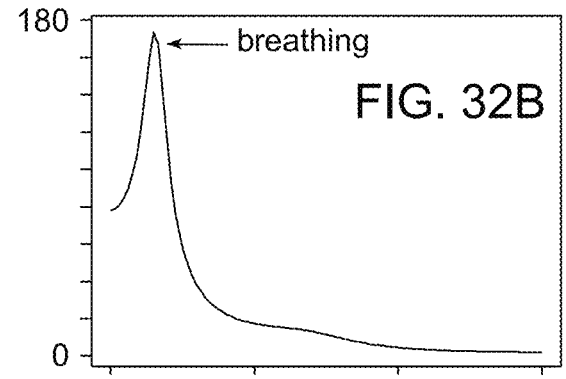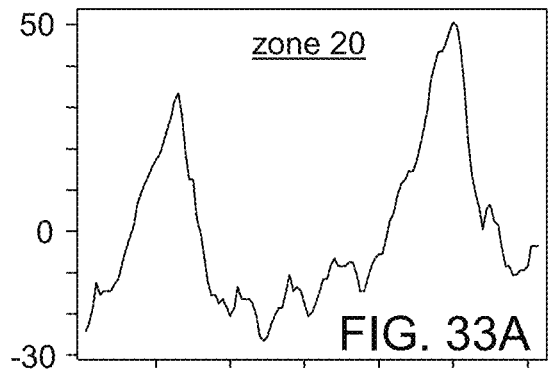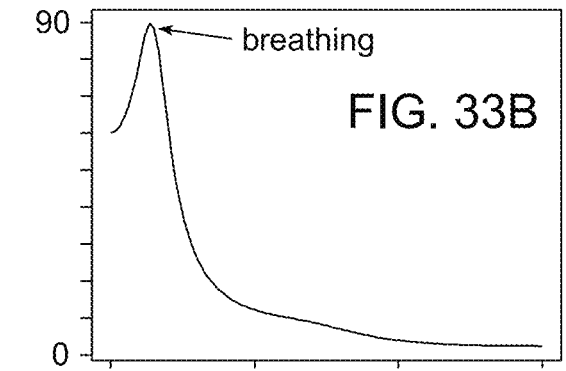

intensity vs frame $(power)^{1/2}$ vs frequency

DETERMINING RESPIRATORY PHASE FROM FLUOROSCOPIC IMAGES

RELATED APPLICATIONS

This application is a continuation-in-part of application Ser. No. 15/891,669 filed on Feb. 8, 2018.

FIELD OF THE INVENTION

This invention is related generally to the field of medical fluoroscopy and more particularly to technology for synchronizing processes and signals with the respiration cycle of a living body.

BACKGROUND OF THE INVENTION

There is a need during some medical procedures, such as in electrophysiology studies, to process images and cardiac electrical signals in synchronization with the respiration of a patient or to selectively base certain processes on the instantaneous phase of the respiration cycle. In electrophysiology, for example, the important issue is the motion of the heart and catheters within the heart which result from respiration and not the actual perfusion of air into the lungs. In such cases, the motion of the diaphragm or lungs or other respiration-driven movement may be of more interest than actual oxygenation of blood, and so estimation of respiratory phase is more particularly directed at tracking the motion of the diaphragm which may occur during respiration or during obstructed apnea or even perhaps during artificial ventilation.

Other methods exist in the art for estimating respiratory phase from fluoroscopic images. For example, U.S. patent application Ser. No. 15/487,245 titled "Rapid 3D Cardiac Parameter Mapping" (Sra et al.), filed on Apr. 13, 2017, discloses a method which estimates respiratory phase by analyzing the motion of an identified cardiac sensor, such as a catheter, placed in the heart. Such method determines the respiratory phase of an image from changes from frame-to-frame in a single coordinate of the positions of the identified sensor.

There is a need for a method which takes advantage of the larger amount of data in an image which contains some information about respiratory phase. When portions of a fluoroscopic image larger than individual objects such as a catheter include anatomic structures such as the diaphragm, ribs or lung which undergo displacement within the image due to respiration, such portions of the image can provide a more reliable indication of respiratory phase than the local motion of an object such as a catheter.

OBJECTS OF THE INVENTION

It is an object of the inventive method of determining respiratory phase of a living body from a sequence of digitized fluoroscopic images of a living-body region exhibiting respiratory displacement to provide an estimate of respiratory phase without the need for a dedicated sensor.

Another object of this inventive method is to determine respiratory phase in a rapid manner such that synchronization of the processing of images and other data such as cardiac electrical signals with respiration can be done rapidly enough to be useful during a medical procedure.

Yet another object of this invention is to provide a method of determining respiratory phase which selects which region of a fluoroscopic image sequence is the best region for such determination.

Yet another object of this invention is to provide a reliable method of determining respiratory phase from a sequence of digitized fluoroscopic images of a region of a living body during a period of time when a contrast dye is being injected into portions of the living-body region.

It is a further object of the present invention to provide a method for determining respiratory phase which will provide a reliable estimate under a wide range of respiratory motion profiles.

Another object of this inventive method is to provide estimates of respiratory phase from which predictions (extrapolated estimates) of respiratory phase may be useful, thereby lowering the total X-ray exposure to a patient during a procedure.

Yet another object of this invention is to provide a method which reduces the effect of X-ray image noise on the estimate of respiratory phase.

These and other objects of the invention will be apparent from the following descriptions and from the drawings.

SUMMARY OF THE INVENTION

The invention is a method of determining respiratory phase of a living body from a sequence of digitized fluoroscopic images of a living-body region exhibiting respiratory displacement. The method employs programmable computing apparatus and comprises the steps of: (a) in each living-body-region image in the sequence, defining one or more zones with each image having identical image-to-image zone locations, sizes, and shapes; (b) for each image, computing an average pixel intensity for each zone to form a sequence thereof for each zone; (c) for each zone, modifying the average pixel intensities by (i) computing the mean value of the sequence of average pixel intensities for such zone, and (ii) subtracting the mean from each average pixel intensity in the zone; (d) for each zone sequence, computing a figure-of-merit; (e) selecting the zone having the highest figure-of-merit; and (f) using the sequence of pixel intensities of the selected zone to determine respiratory phase.

In highly-preferred embodiments of the inventive method, the figure-of-merit for a zone is based on estimates of power spectral density of the sequence of modified average pixel intensities for the zone, and in some of these highly-preferred embodiments, the power spectral density estimates are determined using a maximum entropy method.

In some highly-preferred embodiments, the figure-of-merit is the ratio of power in a predetermined frequency band to the power outside of the predetermined band. In some of these embodiments, the predetermined frequency band is defined by a low frequency $f_1$ and a high frequency $f_2$. In some of these embodiments, $f_1$ is 0.16 Hz and $f_2$ is 0.33 Hz.

In some preferred embodiments of the inventive method, the predetermined frequency band is centered around a prior estimate of respiratory rate, and in some of these embodiments, the prior estimate of respiratory rate is provided by an external signal.

In some other embodiments of the inventive method, the power spectral density estimates are determined using a Fourier transform method.

The term "sizes" as used herein in describing zones within a fluoroscopic image refers only to the amount of area covered by a zone.

The term "external signal" as used herein refers to information provided to the inventive method from a measurement of respiration rate other than from fluoroscopic images.

BRIEF DESCRIPTION OF THE DRAWINGS

FIGS. 1A and 1B together constitute a schematic flowchart of an embodiment of the inventive method of determining respiratory phase of a living body from a sequence of digitized fluoroscopic images of a living-body region exhibiting respiratory displacement. FIG. 1A is a schematic flowchart of method steps which operate on each digitized image in the sequence of images, transforming the image sequence into a set of sequences of scaled average pixel intensity values. Each such numerical sequence is associated with a zone of the fluoroscopic images.

FIG. 1B is a schematic flowchart of method steps which operate on each of the numerical sequences to compute figures-of-merit for each such sequence and to select the best zone from which to determine respiratory phase.

FIG. 4 is a plot of the sequence of average pixel intensities for the zone selected by the method embodiment of FIGS. 1A and 1B, based on the selected zone having the highest figure-of-merit in the example sequence of fluoroscopic images from which the images of FIGS. 2A and 3A were taken.

FIG. 5 is a plot of the sequence of average pixel intensities for another representative zone in the example, such zone having the next-to-highest figure-of-merit.

FIG. 6 is a plot of the sequence of average pixel intensities for a third representative zone in the example, such zone having the lowest figure-of-merit.

FIG. 7 is a plot of the sequence of average pixel intensities for a fourth representative zone in the example, such zone having the next-to-lowest figure-of-merit.

In FIG. 8, this sequence has been smoothed by a moving-window averaging filter having a one-second moving window.

In FIG. 9, this sequence has been smoothed by a moving-window averaging filter having a moving window 0.733 seconds long.

FIG. 13A is a schematic flowchart of method steps which operate on each digitized image in the sequence of images, transforming the image sequence into a set of sequences of scaled average pixel intensity values. Each such numerical sequence is associated with a zone of the fluoroscopic images.

FIG. 13B is a schematic flowchart of method steps of the second embodiment, such steps operating on each of the numerical sequences to compute figures-of-merit for each such sequence and to select the best zone from which to determine respiratory phase.

FIGS. 14A through 38B include 25 pairs of plots (one pair for each of 25 image zone sequences, i.e., M=25 in FIGS. 13A and 13B) of modified average image intensities from an exemplary sequence of fluoroscopic images and the corresponding spectral power densities as represented by the square root of power. In each pair, the "A" figure is the intensity plot and the "B" figure is the power spectral density (PSD) plot (shown as the square root of power).

DETAILED DESCRIPTION OF PREFERRED EMBODIMENTS

FIGS. 1A and 1B are schematic flowcharts (block diagrams) of an embodiment 10 of the inventive method of determining respiratory phase of a living body from a sequence of digitized fluoroscopic images of a living-body region exhibiting respiratory displacement. The flowchart of FIG. 1A illustrates method steps which operate on each digitized image in the sequence of images, transforming the image sequence into a set of numerical sequences of scaled average pixel intensity values. Each numerical sequence is associated with a zone of the fluoroscopic images.

The flowchart of FIG. 1B illustrates method steps which operate on each of the numerical sequences generated in the steps of FIG. 1A to compute figures-of-merit for each such numerical sequence (each zone) and to select the best zone from which to determine respiratory phase.

A sequence of fluoroscopic images is a series of images taken rapidly, typically at a prescribed frame rate. Typical frame rates may be 7.5 or 15 frames per second (fps) but other frame rates may be used depending on the needs of the procedure being performed. The example presented in this document uses data captured at 15 fps; such a frame rate is not intended to be limiting; other frame rates are within the scope of this invention.

Figure 2B:
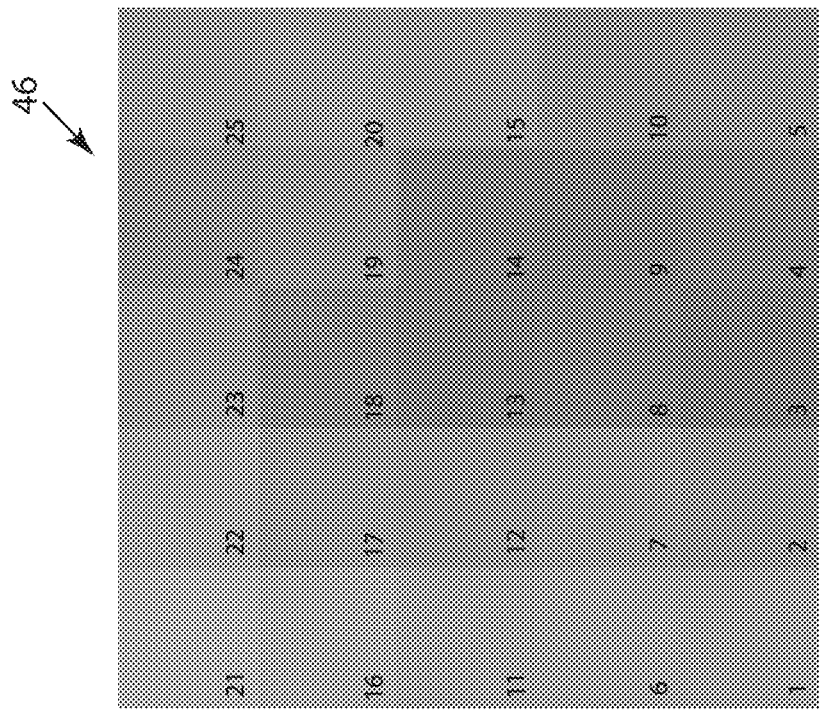
FIG. 2B is a visual illustration of the results of averaging the pixel intensities within each of the 25 zones in the representative frame of FIG. 2A.
Figure 3B:
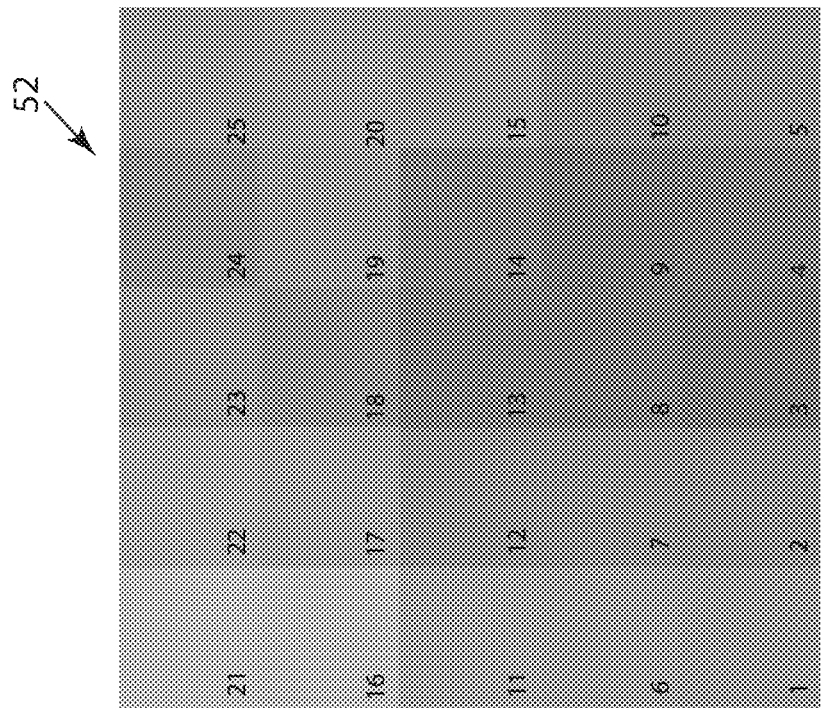
FIG. 3B is a visual illustration of the results of averaging the pixel intensities within each of the 25 zones in the representative frame of FIG. 3A.

The exemplary fluoroscopic images in the example are images having 1,000×1,000 pixels (picture elements). Twenty-five (25) equally-sized square zones are defined in the exemplary images so that each zone is a 200×200 pixel zone. The image resolution and zone configurations of the exemplary images are not intended to be limiting; other image resolutions and zone configurations are within the scope of this invention. In the example, the zone numbering has arbitrarily been chosen as illustrated in FIGS. 2B and 3B.

In the exemplary images, each pixel has a pixel intensity represented by 8 bits such that a totally black pixel has a pixel intensity of 0 and a totally white pixel has a pixel intensity of 255. Such bit resolution or color assignment are again not intended to be limiting.

The method steps of FIGS. 1A and 1B are carried out in automatic computer apparatus. The number of computations in the inventive method and the rate at which such computations must be carried out in order for the method to be useful require that high-speed computational equipment such as programmable computing apparatus must be employed. Such apparatus may include one or more general-purpose computers and/or FPGA devices (field-programmable gate arrays) programmed to carry out the necessary computations and logic of the inventive method. The term "programmable" as used herein is also intended to include fully-custom circuitry designed (programmed) to carry out the computations and logic such that software or firmware are not required as part of such apparatus.

In the flowcharts of FIGS. 1A and 1B, the individual blocks representing the method steps may be referred to herein as method elements.

Referring now to FIG. 1A, method element 12 represents a single digitized fluoroscopic image $I_i$ in a sequence of N images. In the example presented below, the images are as described above, and there are N=148 images in the exemplary sequence. In method step 14, M zones are defined within image $I_i$ such that image $I_i$ is divided into M zones. In the example, there are M=25 equally-sized square zones which form a grid as described above and shown in FIGS. 2B and 3B.

In method element 16, a sum $s_j$ of all of the pixel intensities in each of the M zones ($s_j$ for j=1 to M) is computed. In method element 18, a scaled average pixel intensity $x_j$ is computed for each zone j as $x_j = s_j \cdot c / p_j$ where $p_j$ is the number of pixels in zone j and c is a scaling constant. Note that if no scaling is employed (c=1), the average pixel intensity is the sum $s_j$ divided by the number of pixels $p_j$ in zone j. In the example of this application, there are 40,000 pixels in each zone.

However, scaling may be employed in order to take advantage of some of the extra precision which comes about from using integer arithmetic for the purpose of more rapid computations. In the example presented below, instead of dividing each sum $s_j$ by 40,000, each sum $s_j$ is divided by 8,192 which is rapidly carried out by a simple bit-shifting step since 8,192 is $2^{13}$. In other words, the constant c in the example is c=40,000/8,192=4.8828; each value of average pixel intensity is scaled by a factor of 4.8828. Note that the ordinate of each of the plots in FIGS. 4-9 is scaled in this fashion; thus, average pixel intensity values are well above 255.

Method element 20 simply shows that each image $I_i$ at this stage in method embodiment 10 is represented by a set of M zone values $x_j$ (scaled average pixel intensities), and arrow 22 indicates that since there are N fluoroscopic images in the image sequence, there are M sequences $x_j(I)$ of such N zone values, illustrated by method element 24.

Arrow 25 connects the single-image zone computations of method embodiment 10 in FIG. 1A with the image-sequence zone computations of FIG. 1B. The remaining method steps of method embodiment 10 are computations which lead to figures-of-merit $F_j$ of each of the M zones, evaluated across the entire sequence of N images. The steps of this portion (10 cont'd) of embodiment 10 result in the selection of the best zone from which to determine respiratory phase (or in the special case when M=1, whether or not there is adequate information in the single zone by which to make such a determination).

Referring now to FIG. 1B, method step 26 simply reiterates that in this portion of method embodiment 10, computations are being made on each of the M numerical sequences. In method step 28, mean values $m_j$ for each numerical sequence $x_j(I)$ are computed, and in method element 30, modified numerical sequences $X_j(i)$ are computed by subtracting the mean $m_j$ from each numerical value in the sequence $x_j(i)$, resulting in M modified numerical sequences $X_j(i)$, one for each image in the image sequence.

In method element 32, a sum $A_j$ of the absolute values of the modified numerical sequence $X_j(i)$ is computed, resulting in M values $A_j$, one for each zone. (In method embodiment 10, this sum is specified as being computed for i=2 to N based on later usage of the sum, but a sum from i=1 to N will also be acceptable.) In method element 34, a numerical sequence of first differences $\Delta X_j(i)$ is computed by differencing consecutive values in numerical sequence $\Delta X_j(i) = X_j(i) - X_j(i-1)$ for i=2 to N. Then in method element 36, in similar fashion to method element 32, a sum $B_j$ of the absolute values of the numerical sequence $\Delta X_j(I)$ is computed, resulting in M values $B_j$, one for each zone. (Note that since the first differences are being calculated, method element 34 could alternatively have the unmodified numerical sequence $x_j(i)$ as its input.)

In method element 38, a figure-of-merit $F_j$ is computed for each zone by computing the ratio of and $(K+B_j)$ where K is a constant. The ratio of $A_j$ to $B_j$ basically rewards zones which have the lowest dominant frequency of intensity variation over the entire image sequence. In other words, a higher dominant frequency results in a higher value of the first-difference sum $B_j$ and thus a lower figure-of-merit. The addition of the constant K in the computation of figure-of-merit $F_j$ provides a slight bias toward zones having larger numerical range within their modified numerical sequences $X_j(I)$. If a numerical sequence $X_j(I)$ is thought of as a signal, a larger numerical range within such signal can be described as a stronger signal. (It has been found that a value for K of around 4 adds a small but adequate bias toward larger signals when more than one signal have the same dominant frequency. However, such a value for K is not intended to be limiting. A zero value for K also is possible, but for practical purposes, in the unlikely event that $B_j$ has a value of zero, with a non-zero value for K, a divide-by-zero occurrence is avoided.)

In method step 40, the zone having the highest figure-of-merit $F_j$ is selected as the best zone from which to determine respiratory phase. In method step 42, a smoothing filter is applied to the sequence of scaled average pixel intensities $x_j(i)$ where j is the selected zone number. Flow path 40a indicates that $x_j(i)$ is provided to the filter from method element 26. Finally, respiratory phase is determined in method element 43 from the filtered numerical sequence using techniques well-known to those skilled in signal processing and/or mathematical analysis. It may be as straightforward as identifying the point of maximum inhalation or maximum exhalation. And it is even possible using some methods to determine respiratory phase even if less than an entire respiratory cycle is found in an image sequence. For example, one possible method is to compare even a very brief sequence of average pixel intensity values during a period of increasing or decreasing values with portions of previously-obtained sequences of values as long as the fluoroscope has not been moved relative to the patient.

Figure 2A:
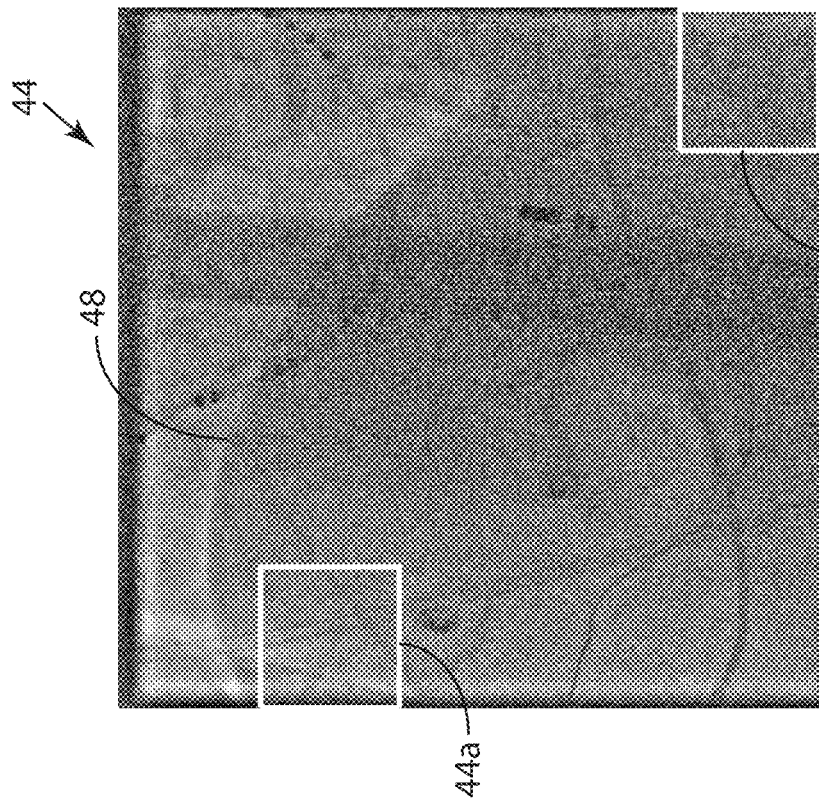
FIG. 2A is a representative frame in a sequence of fluoroscopic images. The fluoroscopic frame of FIG. 2A is taken at a time near the end of exhalation.
Figure 3A:
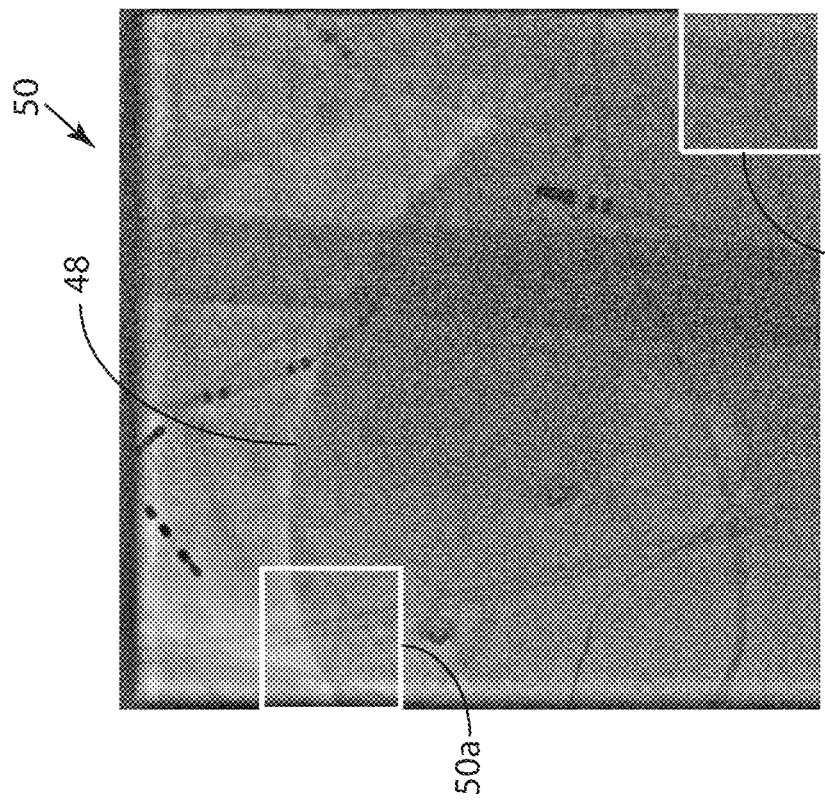
FIG. 3A is another representative frame in a sequence of fluoroscopic images. The fluoroscopic frame of FIG. 3A is taken at a time of maximum inhalation.

FIGS. 2A and 3A are representative fluoroscopic images from an exemplary image sequence of 148 images as introduced above. FIG. 2A is a representative frame 44 at a time near the end of exhalation, and FIG. 3A is a representative frame 50 at a time of maximum inhalation. FIGS. 2B and 3B show depictions 46 and 52, respectively, of the twenty-five zones as defined above with the gray-level shading corresponding to the average pixel intensities as determined by the method of method embodiment 10.

FIG. 2A includes zone 16 and zone 5 marked by reference numbers 44a and 44b, respectively, and FIG. 3A includes zone 16 and zone 5 marked by reference numbers 50a and 50b, respectively. These specific frames are shown to illustrate the much larger change in average pixel intensity that occurs in zone 16 when compared to zone 5. By comparing images 44 and 50 in zone 16, it is easy to see that the motion of a patient's diaphragm 48 is significant in zone 16 while in zone 5, the changes are even difficult to recognize. This illustrates a fundamental feature of the inventive method, that anatomical regions which exhibit respiratory displacement are what are being sensed in the sequence of fluoroscopic images.

Figure 4:
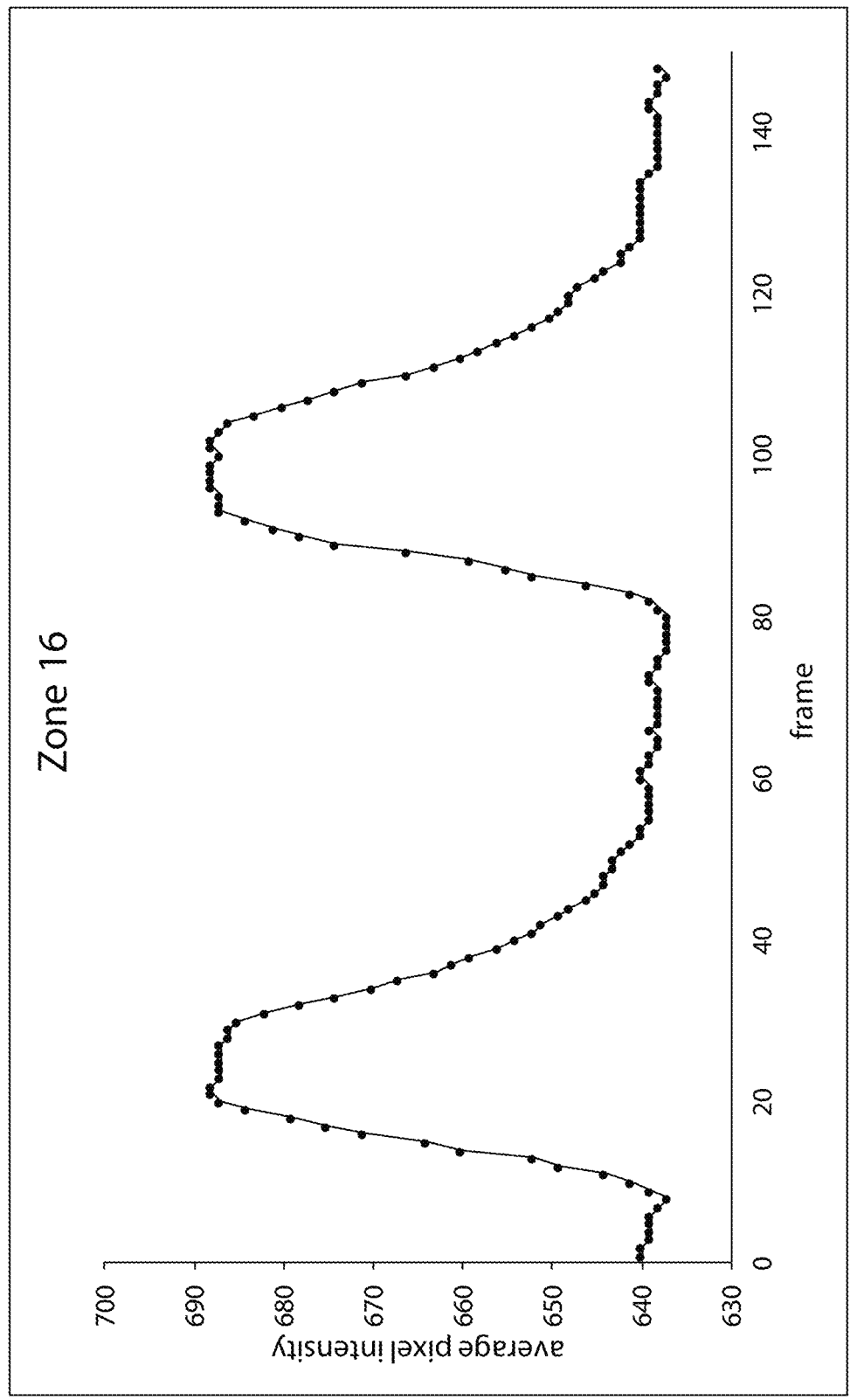
FIGS. 4 through 7 are frame-by-frame plots of sequences of average pixel intensities from four zones in the example sequence of fluoroscopic images from which the images in FIGS. 2A and 3A were taken and as computed by the method of FIG. 1A.
Figure 5:
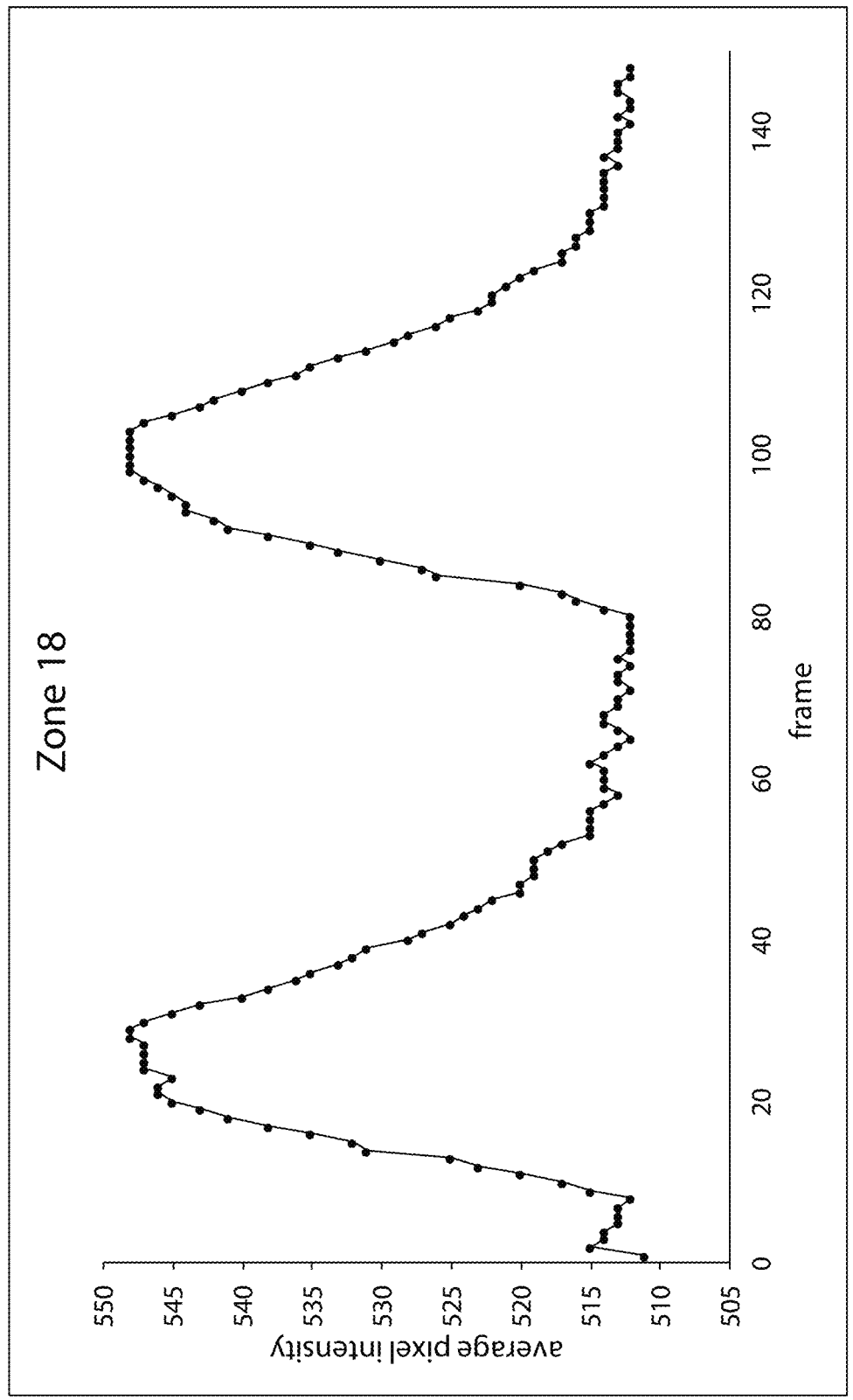
Figure 6:
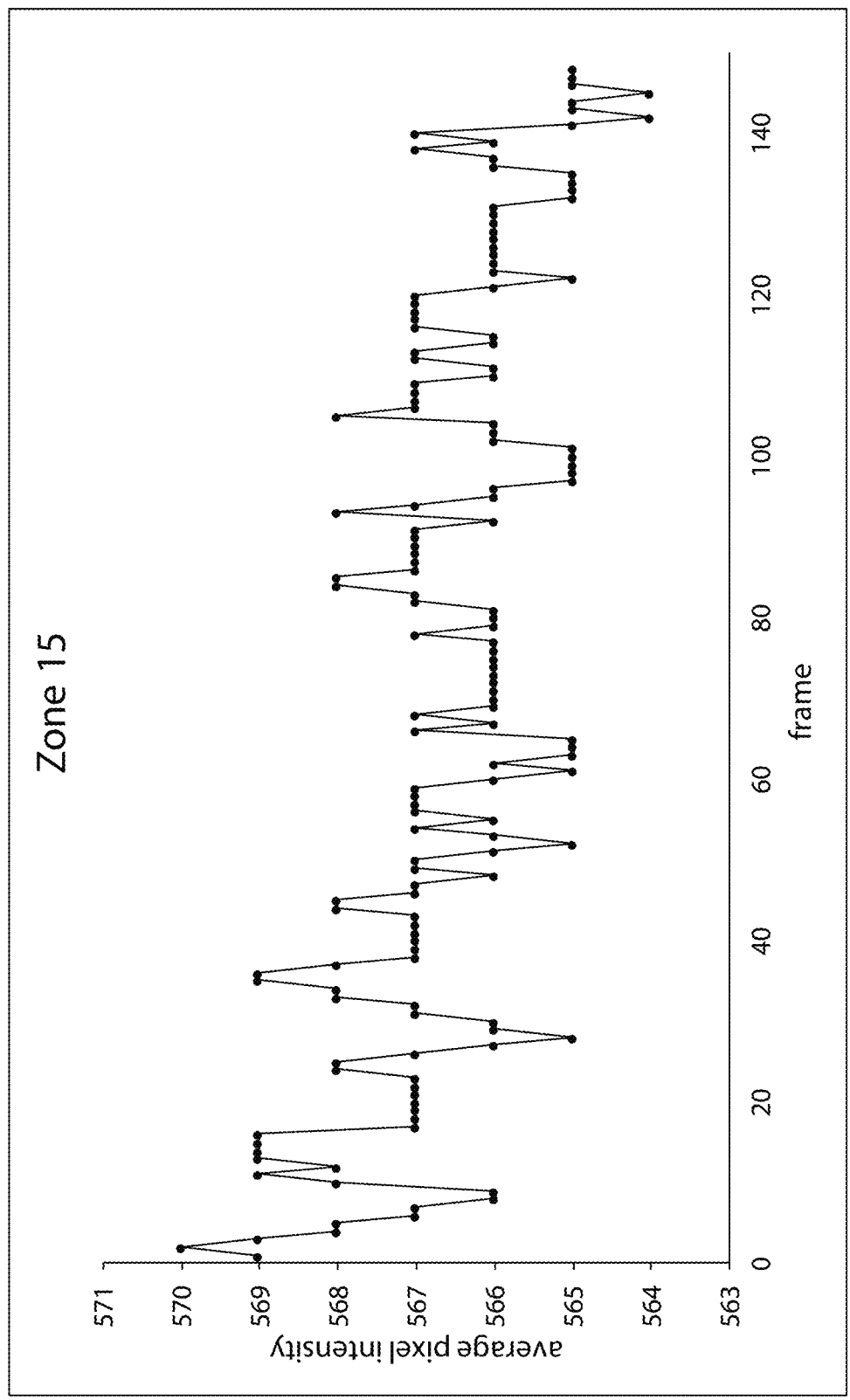
Figure 7:
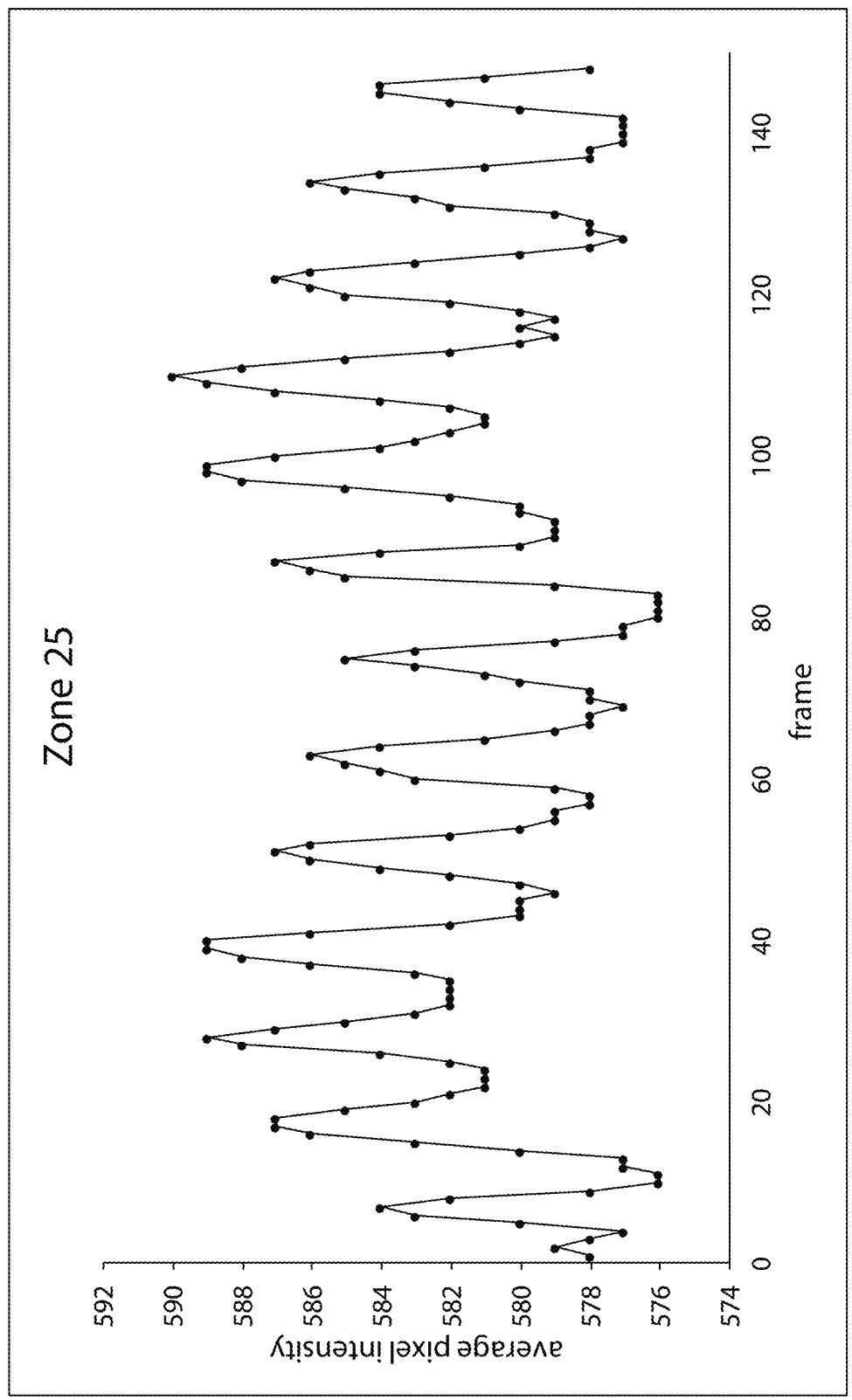

Zone 16 was found in the example to have the highest figure-of-merit ($F_{16}$=11.08) for sequence of 148 images. FIG. 4 is a frame-by-frame plot of the scaled average pixel intensity for zone 16 in the example. As points of comparison, FIG. 5 is a frame-by-frame plot of the scaled average pixel intensity for zone 18 in the example, FIG. 6 is a frame-by-frame plot of the scaled average pixel intensity for zone 15, and FIG. 7 is a frame-by-frame plot of the scaled average pixel intensity for zone 25. Zone 18 was found to have the next-to-the-highest figure-of-merit (9.83), zone 15 was found to have the lowest figure-of-merit (1.74), and zone 25 was found to have the next-to-the-lowest figure-of-merit (1.95). (Note that in making comparisons among the plots of FIGS. 4-7, one should also take into account the range of values along which the scaled average pixel intensities vary.)

Figure 8:
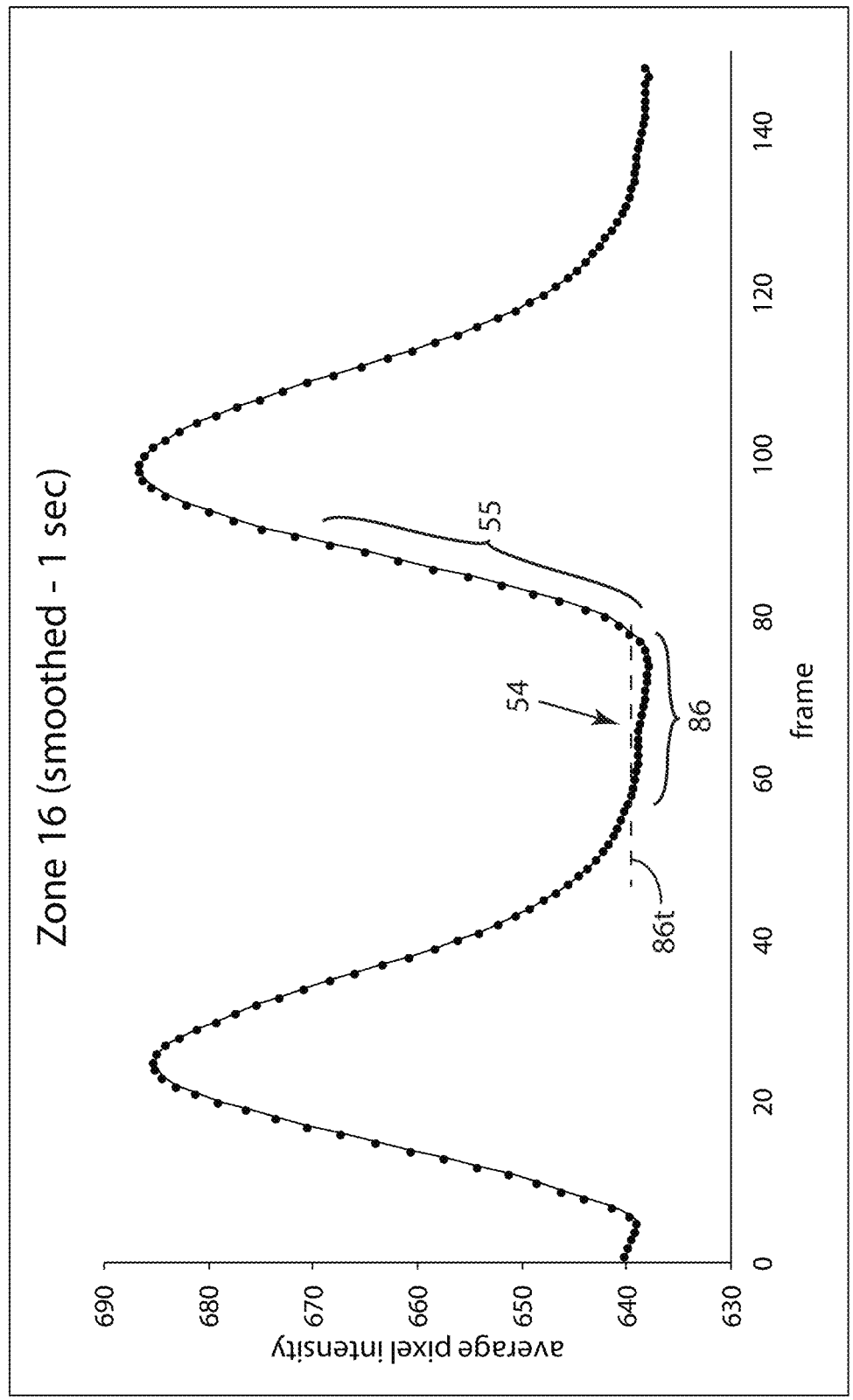
FIG. 8 is a plot of the sequence of FIG. 4, such sequence being the selected zone.
Figure 9:
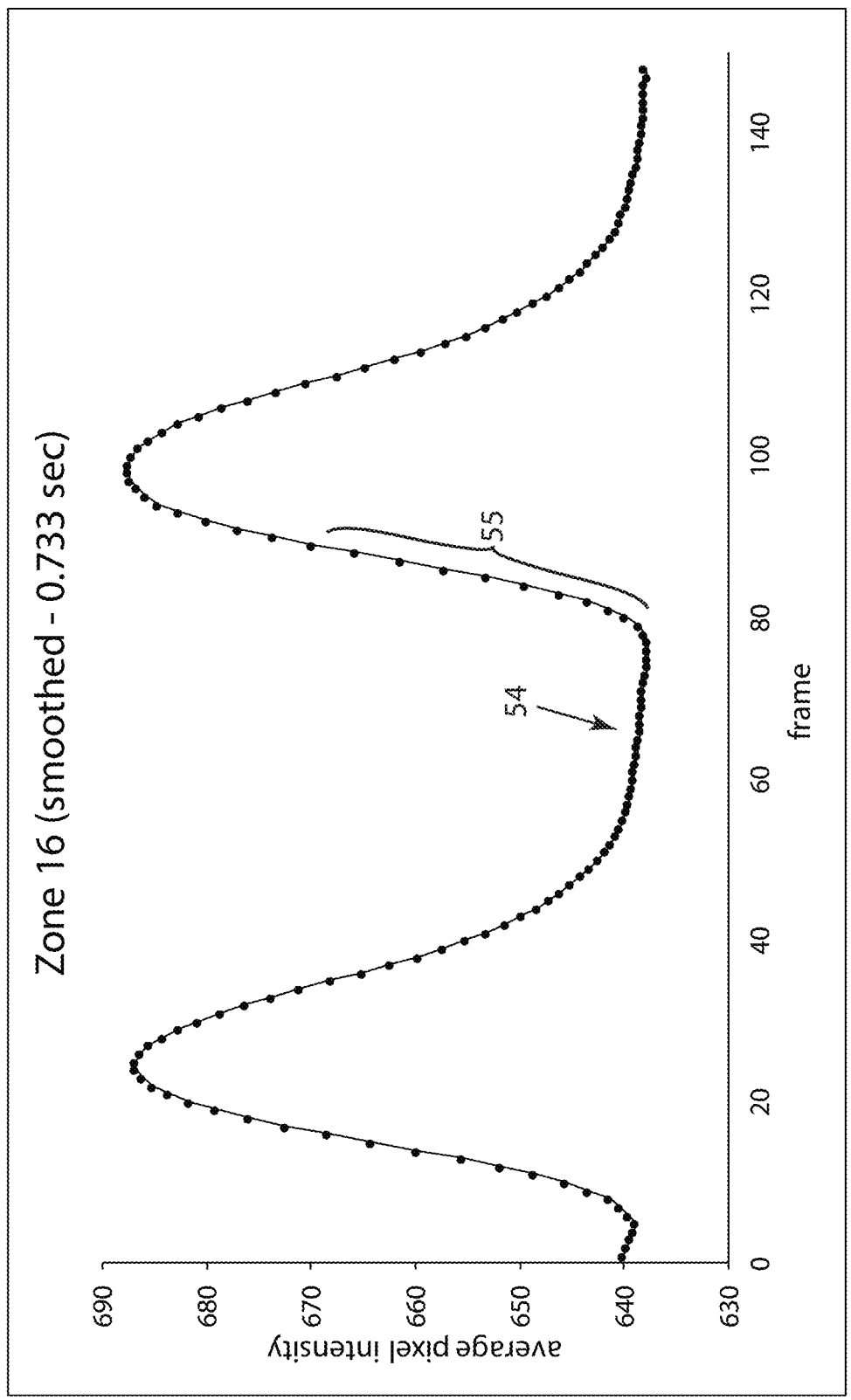
FIG. 9 is a plot of the sequence of FIG. 4, such sequence being the selected zone.

FIG. 8 is a frame-by-frame plot of the scaled average pixel intensity of FIG. 5 to which a one-second moving-window averaging filter has been applied. Moving-window averaging is well-known to those skilled in signal processing and need not be described in detail herein. FIG. 9 is a frame-by-frame plot of the scaled average pixel intensity of FIG. 5 to which a moving-window averaging filter having a moving window 0.733 seconds long (11 frames) has been applied. The 0.733 second moving-window was determined from a measurement of the cardiac cycle within the 148-image sequence. By comparing regions 54 in FIGS. 8 and 9, one can see slightly more effective filtering of the cardiac motion from the signal. As is well-known, smoothing becomes more important in the presence of more image noise, and in the case of determining the moving-window size from the cardiac cycle, the purpose of such filtering is to remove the cardiac cycle, not X-ray noise, from the scaled average pixel intensity signal as much as possible without corrupting the respiratory phase determination. One advantage of removing the cardiac cycle can be seen in the comparison between FIGS. 8 and 9 by observing the steeper leading edge 55 of the respiratory cycle which is evident in FIG. 9.

While the example presented herein includes a very useful definition of zones within images, it is noted that within the scope of the present inventive method, (1) fluoroscopic images need not be square, (2) zones need not be square or rectangular, (3) zones need not have identical sizes (areas), (4) zones need not have identical shapes, and (5) zones need not completely cover the area of the image. The key parameters within the inventive method relate to the average pixel intensities within zones, and zone definitions which provide good assessments of average pixel intensities of the zones are all that is required. FIGS. 10A-10F are schematic illustrations of some variations of zone definitions within fluoroscopic images which may be processed by the inventive method, and the variations illustrated therein are not intended to be limiting. Each of the exemplary illustrations in FIGS. 10A-10F include zones which are non-overlapping. Any regions of two or more zones which overlap cause possible lowering of the differences between the values of the figures-of-merit for the overlapping zones.

Figure 10A:
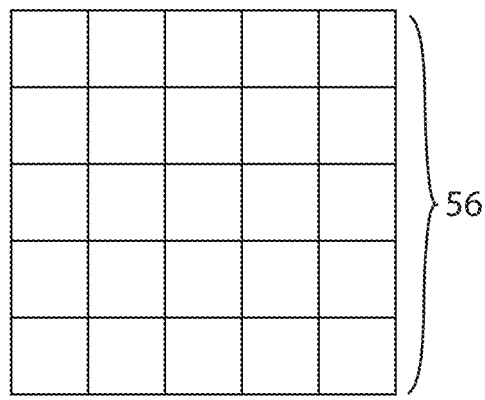
FIGS. 10A-10F are schematic illustrations of variations of zone definitions within fluoroscopic images processed by the inventive method.

FIG. 10A illustrates the simple zone definition 56 of the example described in detail above—twenty-five square zones completely covering the image area. FIGS. 10C and 10E illustrate two more zone definitions which completely cover the image area. FIG. 10C illustrates a zone definition 60 in which the zones all have identical sizes (areas) and shapes (rectangular), and FIG. 10E illustrates a zone definition 64 in which both the sizes (areas) and shapes of the zones differ.

Figure 10B:
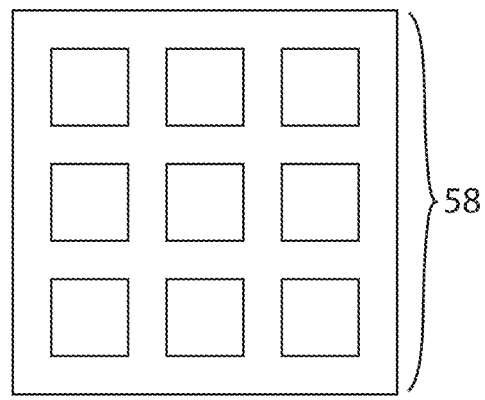
Figure 10C:
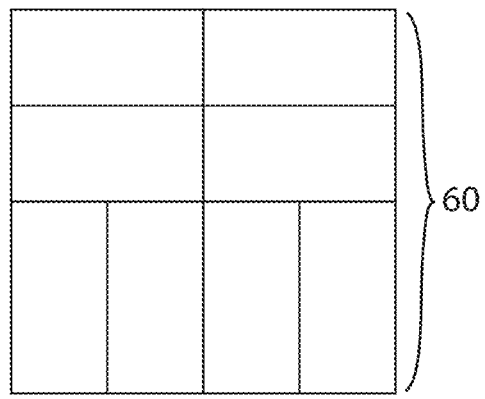
Figure 10D:
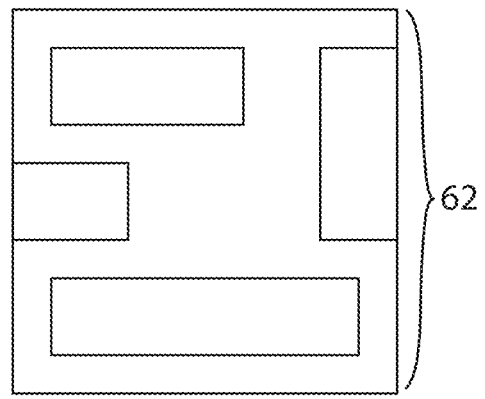
Figure 10E:
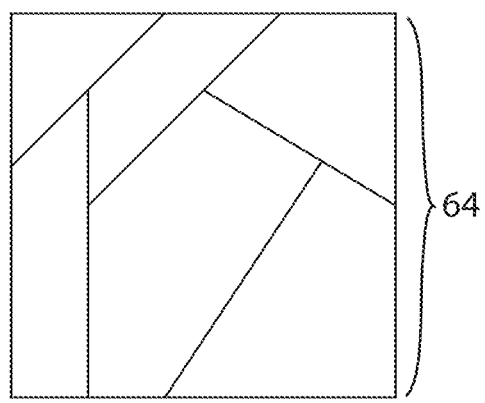
Figure 10F:
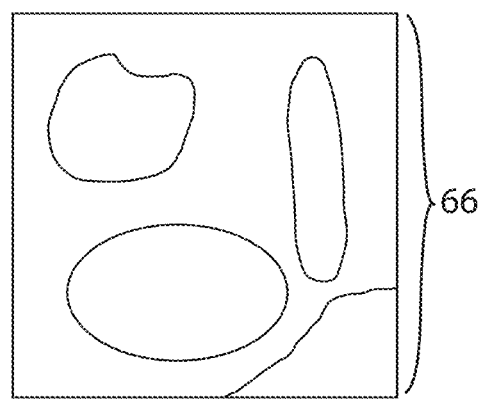

FIGS. 10B, 10D and 10F illustrate zone definitions which do not completely cover the image area. Zone definition 58 of FIG. 10B includes nine identical square zones; zone definition 62 of FIG. 10D includes four rectangular zones which have different sizes (areas) and shapes (aspect ratios); and zone definition 66 of FIG. 10F includes four irregularly-shaped zones having different sizes (areas). One example of a situation in which only partial coverage of an image may be helpful is when a fluoroscopic system places text in an image (usually near an edge of the image) that changes image-to-image.

Note that the zone definition of any of the zone definitions which do not completely cover the image area could be modified by also defining the remaining image area as an additional zone.

Of course, from a practical point-of-view, the ease and speed with which the attendant computations can be carried out are also important considerations in the step of defining zones within an image. Many of the exemplary options for zone definitions set forth in FIGS. 10A-10F will likely not satisfy such practical considerations.

Figure 11:
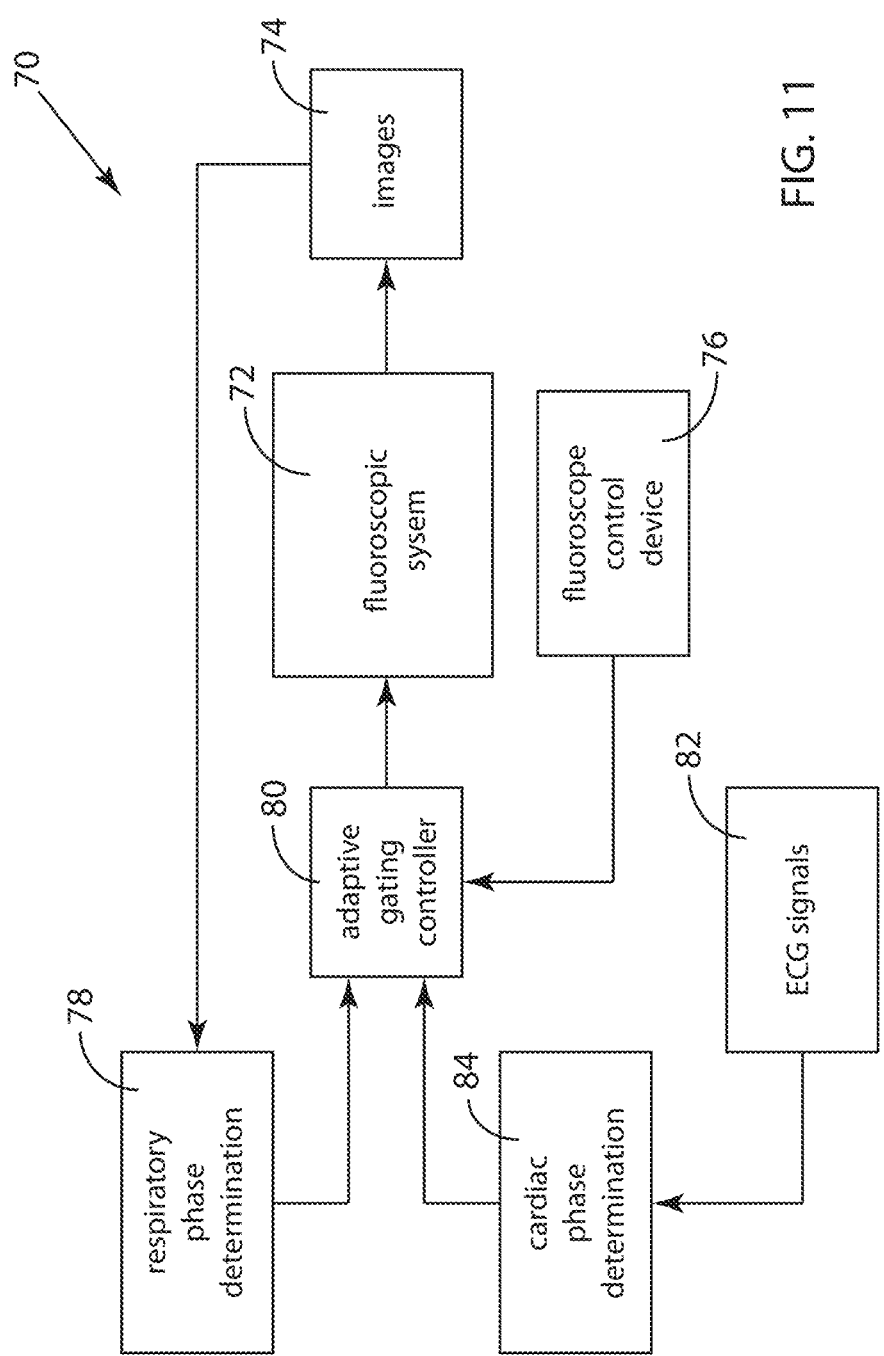
FIG. 11 is a schematic flowchart of a system which combines the inventive method of respiratory phase determination of FIGS. 1A and 1B with method steps which control the activation of a fluoroscopic system based on respiratory phase and cardiac phase.

FIG. 11 is a schematic flowchart of an embodiment 70 of an inventive method which combines an embodiment of the inventive method of respiratory phase determination (such as embodiment 10 of FIGS. 1A and 1B) with method steps which control the activation of a fluoroscopic system 72 based on respiratory phase and cardiac phase. Fluoroscopic system 72 is controlled by an adaptive gating controller 80 which is controlled by a fluoroscope control device 76. Fluoroscope control device 76 may be a pedal 76 or a foot switch 76 or other convenient switching device such as a voice recognition module 76. Most typically, fluoroscope control device 76 is a pedal; thus for convenience and simplicity, hereinafter in this description of FIG. 11, fluoroscope control device 76 will be referred to as pedal 76. The use of term pedal 76 in this fashion is not intended to be limiting; many other switching devices are contemplated as being within the scope of this invention.

Pedal 76 is an ON/OFF switching device which sends an ON/OFF signal to controller 80 to indicate that pedal 76 is either pressed (ON) or not pressed (OFF). While pedal 76 is sending an ON signal to controller 80, controller 80, using respiratory phase information from method element 78

(from method steps such as in exemplary embodiment 10 illustrated in FIGS. 1A and 1B), compares a target respiratory phase region 86 (see FIG. 8) and an estimate of current respiratory phase to determine whether or not to send an ON or OFF signal to fluoroscopic system 72 which will either start or stop the stream of fluoroscopic images being generated. Thus, when pedal 76 is in an ON position, controller 80 may either delay the start of the generation of fluoroscopic images or advance the stopping of image generation, relative to the signal being sent by pedal 76.

Referring again to FIG. 8, target respiratory phase region 86 may be defined by respiratory phases below a phase threshold 86t as indicated by a dotted line 86t. Target respiratory phase region 86 includes times (frames) along the respiratory timeline as represented by the smoothed average pixel intensity curve of FIG. 8 during which the estimated respiratory phase is below phase threshold 86t.

FIG. 11 also includes a method element 84 which represents a determination of cardiac phase derived from a set of ECG signals 82. Both respiratory and cardiac phase information may be combined within controller 80 to provide an even more intelligent gating signal to fluoroscopic system 72. Cardiac phase determination method element 84 may include cardiac phase determination methods well-known to those skilled in the area of signal processing and are not described here in detail.

Figure 12A:
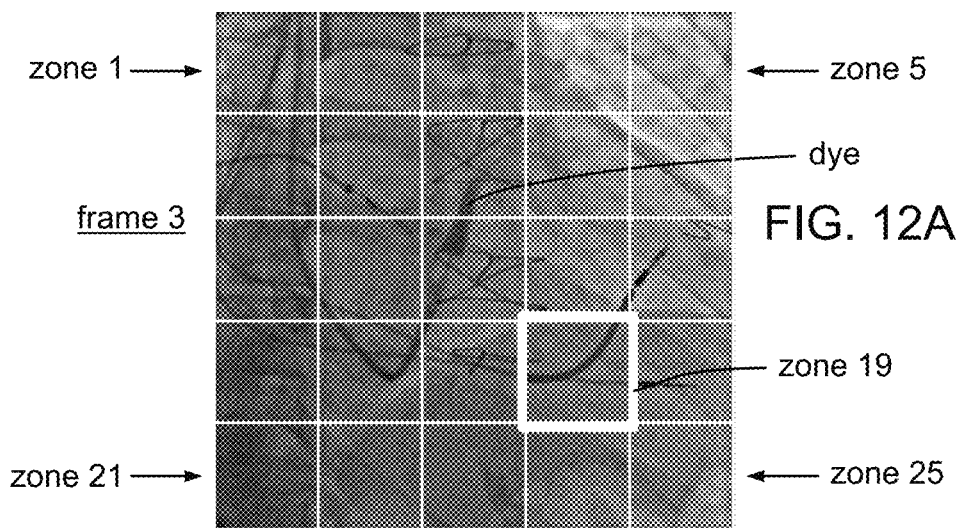
FIGS. 12A through 12C are three representative frames from a sequence of fluoroscopic images.
Figure 12B:
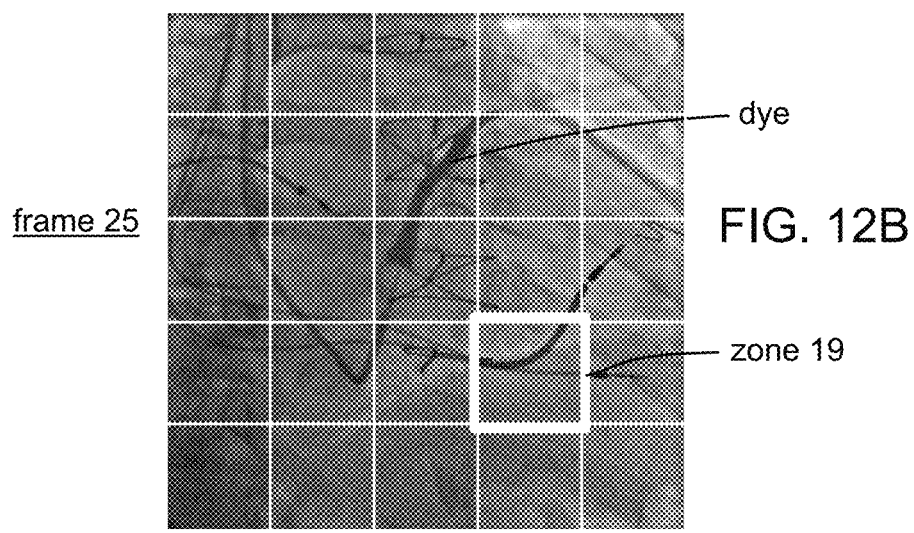
Figure 12C:
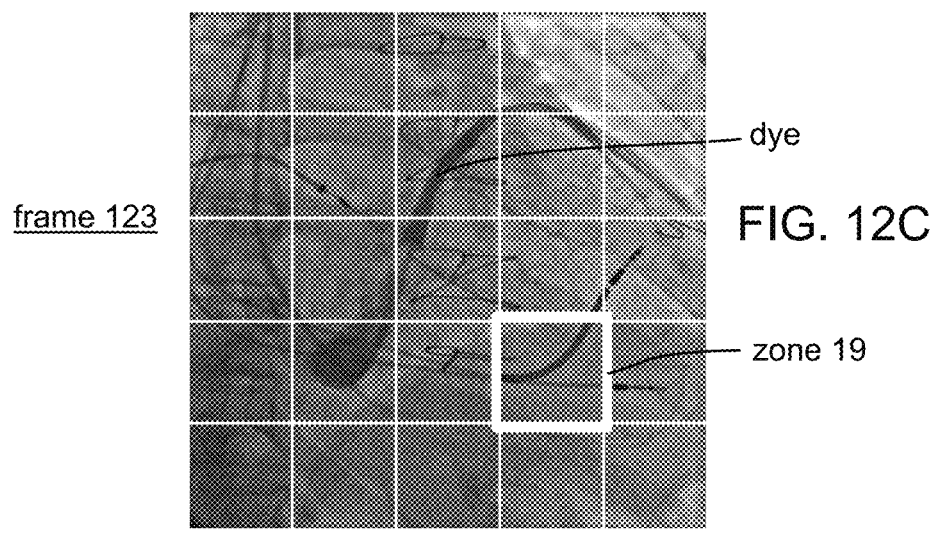

It has been found when applying the method of embodiment 10 in situations in which there are time-varying disturbances in the fluoroscopic images that the method of embodiment 10 may not yield reliable estimates of respiratory phase due to selecting an inappropriate zone from which to determine phase. This type of situation may occur when contrast dye is introduced into various blood vessels, such as may occur during a cardiac angiogram. FIGS. 12A through 12C are three representative frames from such a sequence of fluoroscopic images. The sequence runs from frame 3 to frame 123; the first two frames are start-up frames and are typically not usable. The images each contain one million pixels (1000×1000 pixels), and the frame rate is 15 frames per second. Thus, the sequence of images is just over 8 seconds long. The three frames shown in FIGS. 12A-12C are frame 3, frame 25 and frame 123. Note that in this example the zone numbering starts in the upper left corner of the images rather than the lower left, as in the previous example in this document.

FIGS. 12A-12C also indicate the introduction of contrast dye in the images of frames 3, 25 and 123. Zone 19 is highlighted for later reference. Frame 3 (FIG. 12A) illustrates minimum dye injected and a relaxed diaphragm due to exhaled breath. Frame 25 (FIG. 12B), illustrates partial dye injection and a lowered diaphragm at a point of maximum inhaled breath. Frame 123 (FIG. 12C) illustrates maximum dye injection and a relaxed diaphragm after a second breath.

Figures 13A, 13B:
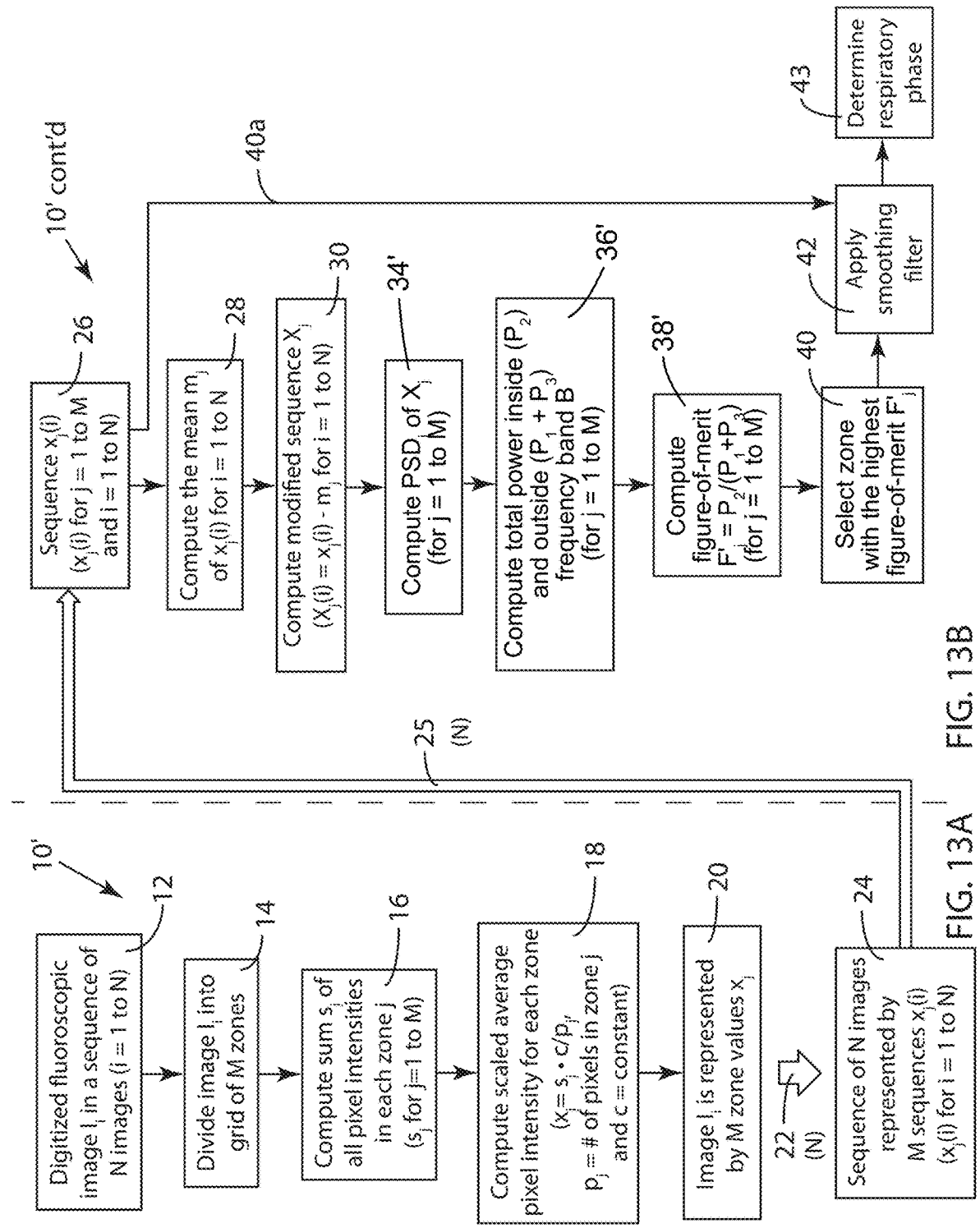
FIGS. 13A and 13B together constitute a schematic flowchart of a second embodiment of an inventive method of determining respiratory phase of a living body from a sequence of digitized fluoroscopic images of a living-body region exhibiting respiratory displacement. The second embodiment employs a figure-of-merit based on estimates of power spectral densities of image sequences.
Figure 22A:
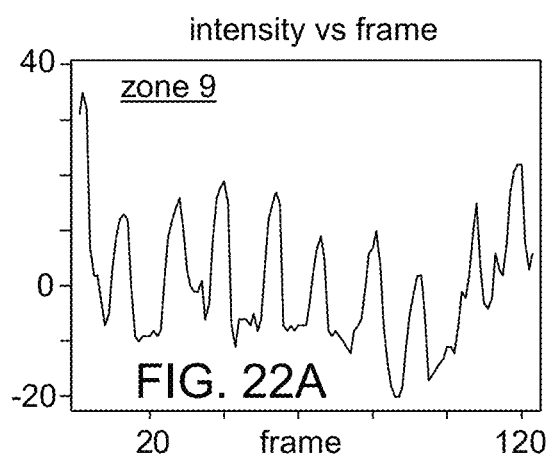
Figure 22B:
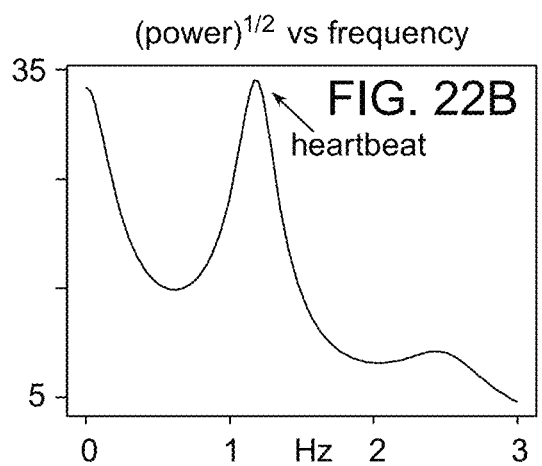
Figure 23A:
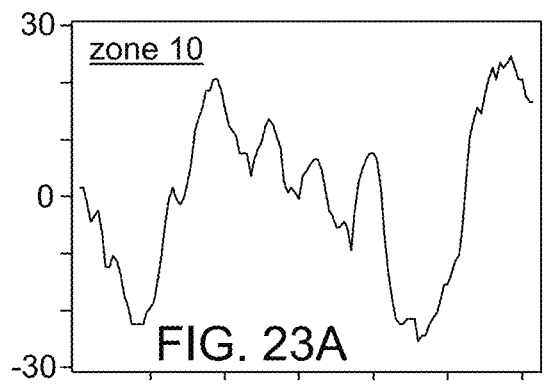
Figure 23B:
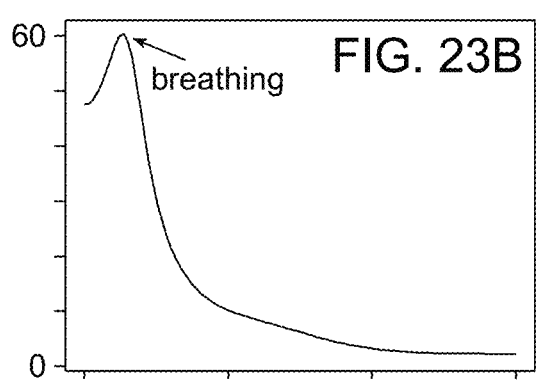
Figure 24A:
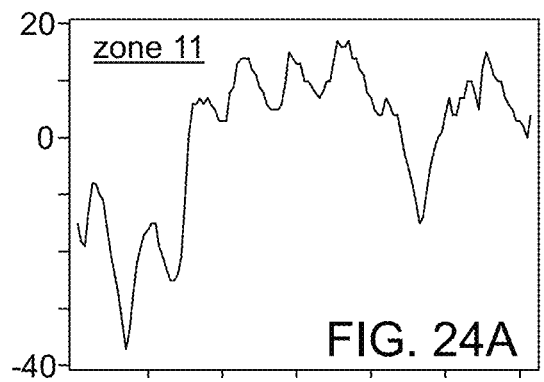
Figure 24B:
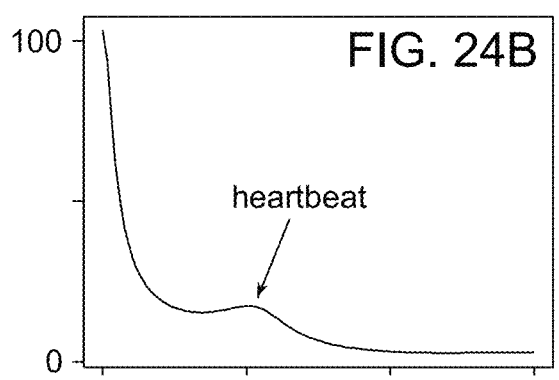
Figure 25A:
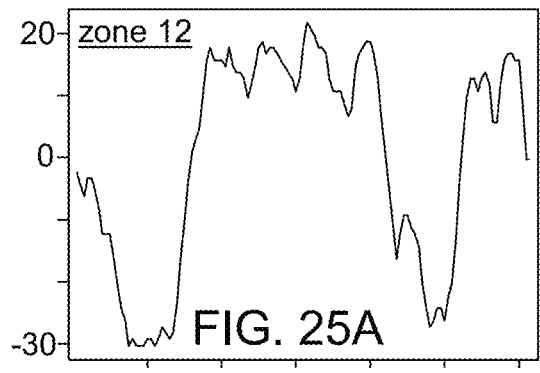
Figure 25B:
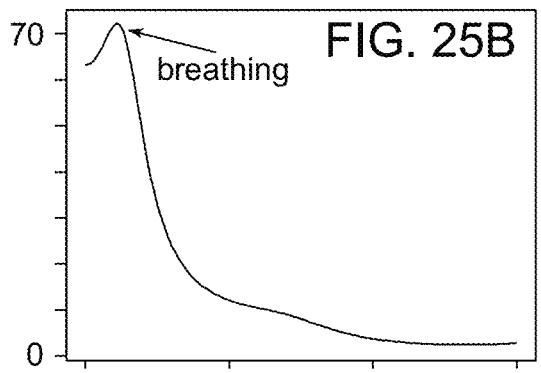
Figure 26A:
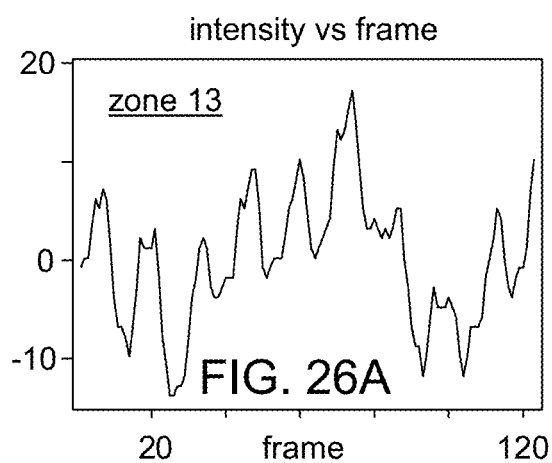
Figure 26B:
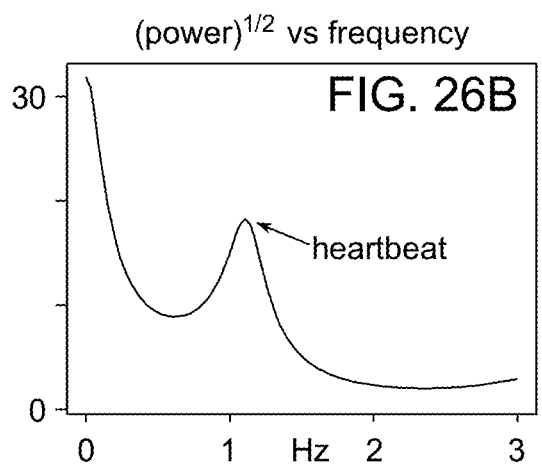
Figure 27A:
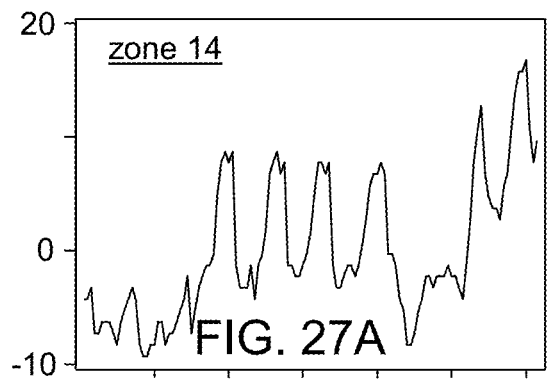
Figure 27B:
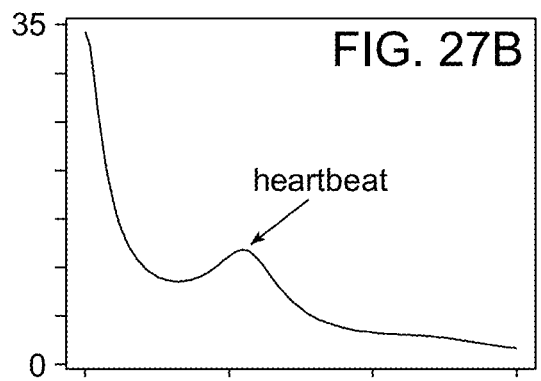
Figure 28A:
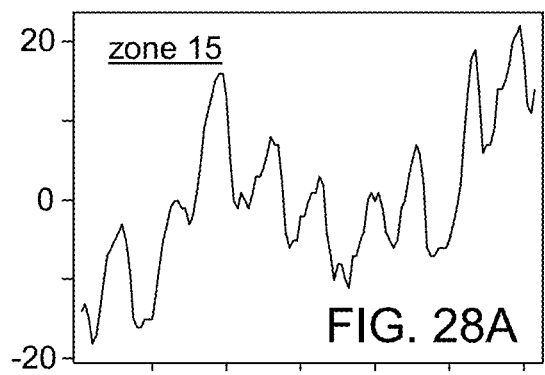
Figure 28B:
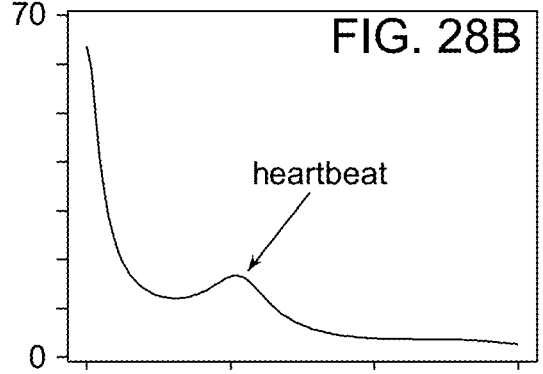
Figure 29A:
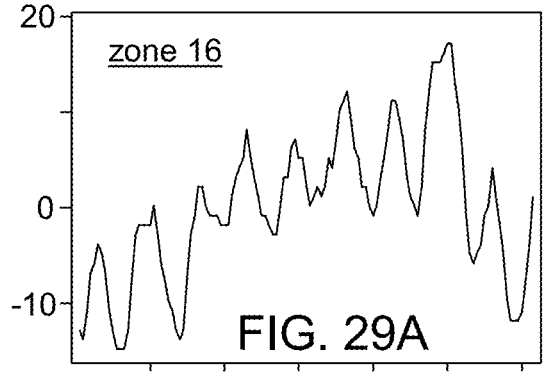
Figure 29B:
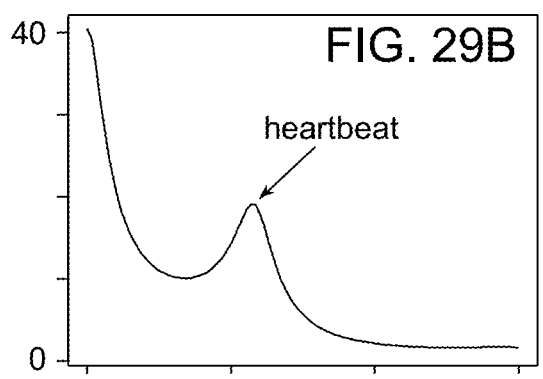
Figure 34A:
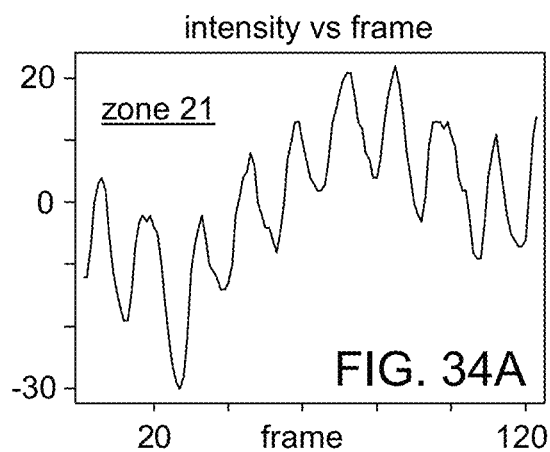
Figure 34B:
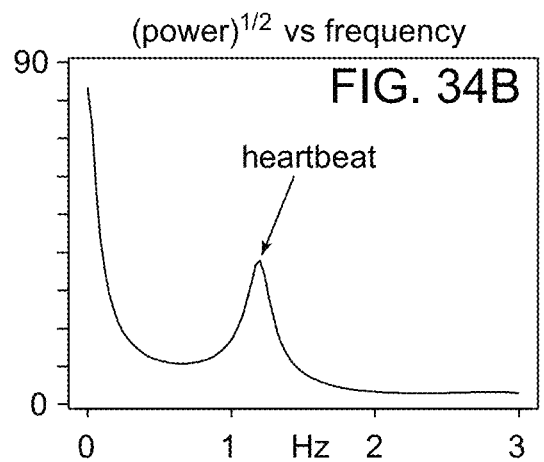
Figure 35A:
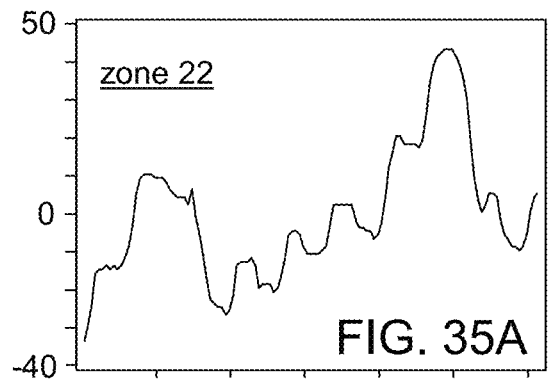
Figure 35B:
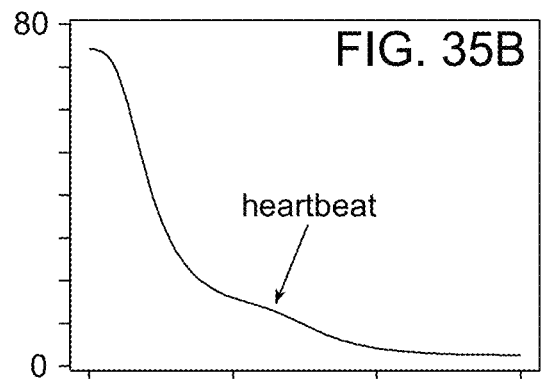
Figure 36A:
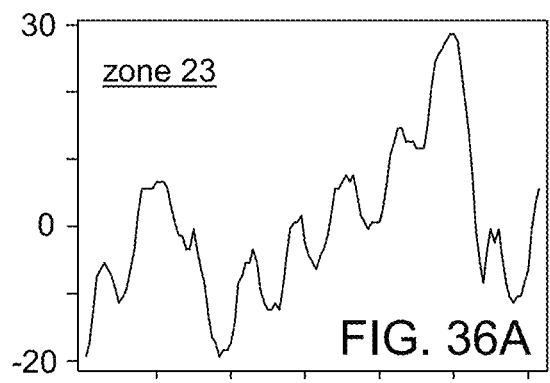
Figure 36B:
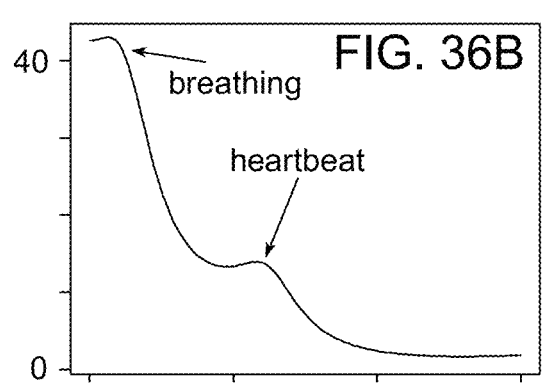
Figure 37A:
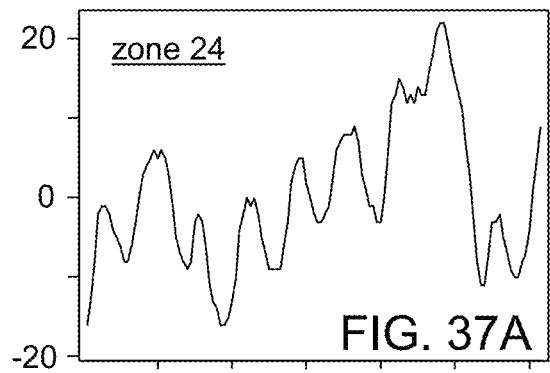
Figure 37B:
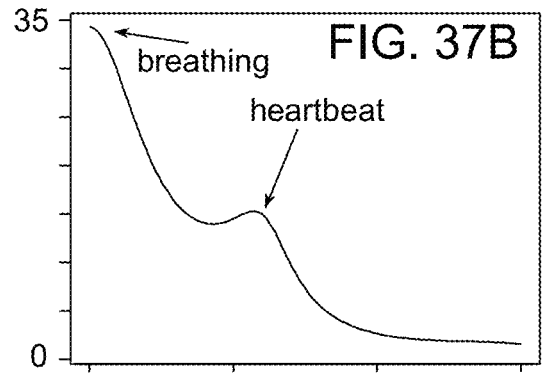
Figure 38A:
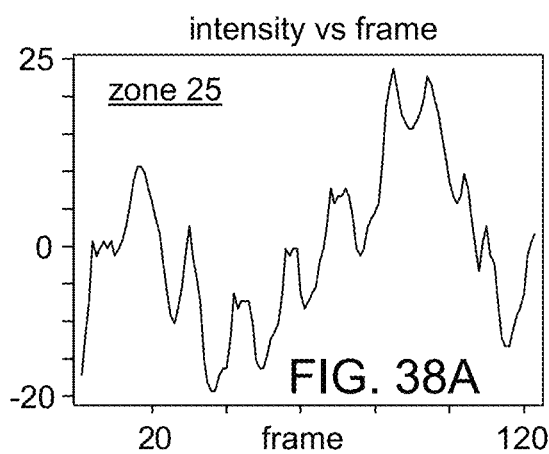
Figure 38B:
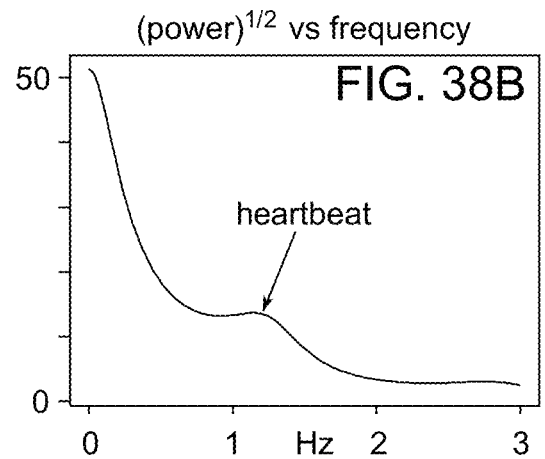

FIGS. 13A and 13B together constitute a schematic flowchart of a second embodiment 10' of a method of determining respiratory phase of a living body from a sequence of digitized fluoroscopic images (i being the frame or image number—there are N sequential images) of a living-body region exhibiting respiratory displacement. Embodiment 10' employs a figure-of-merit $F'_j$ (j being the zone number) for each zone which is based on estimates of a power spectral density $PSD_j$ of each zone sequence $x_j(i)$.

FIG. 13A is identical to FIG. 1A, and the description of FIG. 13A is therefore found in previous sections of this document. Thus, descriptions of method elements 12, 14, 16, 18, 20, 22, 24 and 25 are the same as found above.

FIG. 13B is a schematic flowchart of method steps of second embodiment 10' which operate on each zone sequence to compute figures-of-merit $F'_j$ resulting in figures-of-merit from which to select the best zone for respiratory phase determination. Method elements 26, 28, 30, 40, 42 and 43 are identical to the corresponding elements in FIG. 1B, and these descriptions are found above in this document.

In FIG. 13B, method elements 34', 36' and 38' are different from the corresponding elements in embodiment 10. In method element 34', power spectral densities $PSD_j$ for j=1 to M (M is 25 in the example) are computed. One preferred method for computing $PSD_j$ is known as the maximum entropy method and is well known to those skilled in the field of signal processing and need not be detailed here. For the calculations used in the example presented in FIGS. 14A through 41, a maximum entropy method employed a model of using 10 poles, but the use of such a model is not intended to be limiting. Other approaches can be used to calculate power spectral densities PSD such as a Fourier transform. For example, it is known that the Fourier transform of the autocorrelation of the zone intensity sequences yields the PSD of such a sequence.

Before continuing the description of embodiment 10' in FIG. 13B, it is useful to describe FIGS. 14A through 38B and FIG. 39. FIGS. 14A through 38B include 25 pairs of plots (one pair for each of the 25 zone image sequences, i.e., M=25 in FIGS. 13A and 13B) of modified average image intensities $X_j(i)$ for i=1 to N from an exemplary sequence of fluoroscopic images $I_i$ and the corresponding spectral power densities $PSD_j$ as represented by the square root of power. In each pair, the "A" figure is the intensity plot, and the "B" figure is the power spectral density (PSD) plot (shown as the square root of power). In subsequent calculations, power rather than the square root of power is used. However, the "B" plots 14B-38B are presented in square root form herein simply to illustrate more easily the presence of breathing and heartbeat signals in the power spectral density values. The square root serves to accentuate such signals, particularly the heartbeat signal, and is therefore useful in understanding how the inventive method performs. Breathing and heartbeat features are labeled in some of the "B" plots in FIGS. 14B-38B to illustrate this point; such features are not as easily identified in plots of power versus frequency. (Compare FIG. 32B with FIG. 39 in the region of frequency, near 1.3 Hz, in which a "heartbeat" feature is only weakly evident in FIG. 32B and not in FIG. 39.)

Note that all of the "A" plots in FIGS. 14A-38A have the same abscissa scale and thus, for simplicity, such a scale is shown only once on each page containing these plots. The same is also true for all of the "B" plots in FIGS. 14B-38B.

Figure 39:
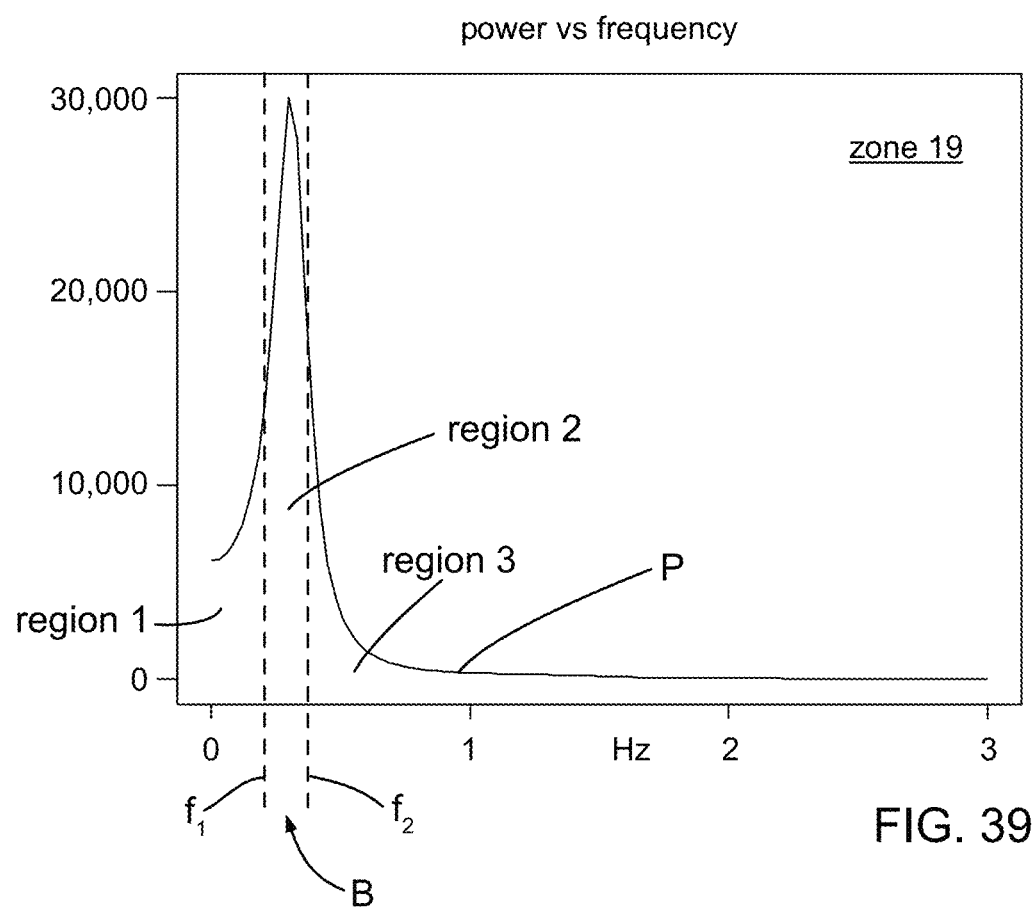
FIG. 39 is a representative power versus frequency plot for one of the zones—zone 19 from FIGS. 32A and 32B—but now plotted as power rather than the square root of power.

FIG. 39 is a representative power versus frequency plot for one zone 19 from FIGS. 32A and 32B—now plotted as power since all of the calculations in embodiment 10' use power P rather than the square root of power. (Note that FIGS. 12A-12C each have zone 19 highlighted for convenient reference.) FIG. 39 illustrates that each PSD is divided into three regions defined by a predetermined frequency band B defined by a low frequency $f_1$ and a high frequency $f_2$. $P_1$ is the total power under power plot P within region 1, i.e., below frequency $f_1$; $P_2$ is the total power under power plot P within region 2, i.e., between frequency $f_1$ and frequency $f_2$; and $P_3$ is the total power under power plot P within region 3, i.e., above frequency $f_2$. In other words, these total power values are determined by numerically integrating power density P within their corresponding frequency ranges.

Referring again to FIG. 13B, method element 36' represents such calculations of $P_1$, $P_2$ and $P_3$ for each of the M zones (M=25). Then in method element 38', a figure-of-merit $F'_j$ (one for each of M zones) is calculated as the ratio $P_2/(P_1+P_3)$. In other words, figure-of-merit $F'_j$ is calculated as the ratio of power within predetermined frequency band B (between frequency $f_1$ and frequency $f_2$) and the power outside of frequency band B.

Predetermined frequency band B may be established several ways. A normal free-breathing, non-talking, resting human will breathe about once every four to five seconds. Thus, frequency band B may simply be set by setting low frequency $f_1$ and high frequency $f_2$ at values which surround such frequencies while avoiding higher frequencies such as normal cardiac rates more typically around 1 Hz. Useful values for $f_1$ and $f_2$ may be about 0.167 and 0.333, respectively; these values correspond to breathing rates between one breath every 3 to 6 seconds ($f_1$=0.167 Hz and $f_2$=0.333 Hz).

Frequency band B may also be determined by a signal which is provided by another system (an external signal source different from fluoroscopic images) and then frequencies $f_1$ and $f_2$ may be set to be centered around a respiratory rate provided by such an external source.

As stated above, method elements 40, 42 and 43 are identical to those in embodiment 10 and need not be described here.

Figure 41:
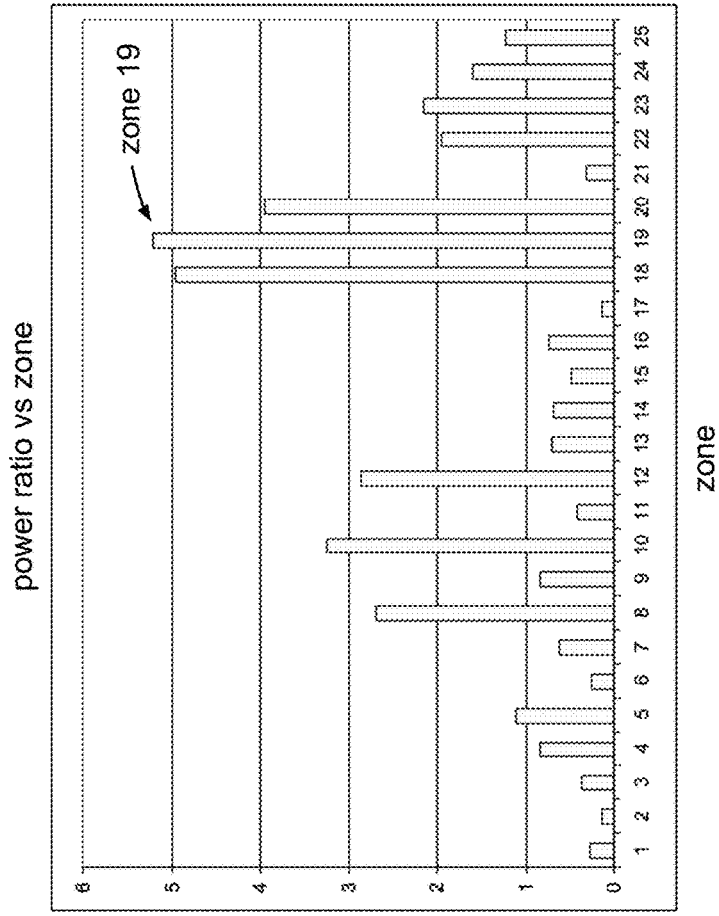
FIG. 41 is a bar chart of the results shown in the table of FIG. 40.
Figure 40:
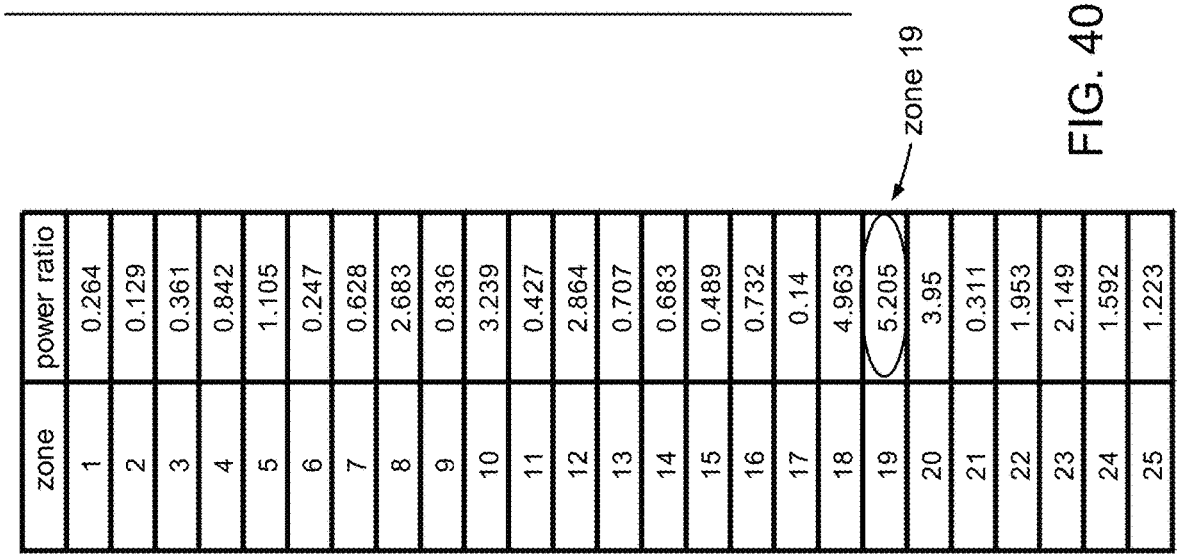
FIG. 40 is a table of figures-of-merit resulting from the calculations performed on the exemplary sequence of images represented by the plots of FIGS. 14A through 38B and described in FIGS. 13A and 13B.

FIG. 40 presents a table of figures-of-merit $F'_j$ for j=1 to 25 resulting from the calculations performed as outlined above with method embodiment 10' on the exemplary sequence of images represented by the plots of FIGS. 14A through 38B and described in FIGS. 13A and 13B. FIG. 41 is simply a bar chart of the results shown in the table of FIG. 40. As shown, zone 19 is the zone having the highest figure-of-merit F' in this example, and experience has shown that even with the introduction of contrast dye during the exemplary image sequence, embodiment 10' reliably estimated respiratory phase while the method of embodiment 10 had considerable difficulty with this sequence of images.

While the principles of this invention have been described in connection with specific embodiments, it should be understood clearly that these descriptions are made only by way of example and are not intended to limit the scope of the invention.

The invention claimed is:

1. A method of determining respiratory phase of a living body from a sequence of digitized fluoroscopic images of a living-body region exhibiting respiratory displacement, the method employing programmable computing apparatus and comprising the steps of:
    in each living-body-region image in the sequence, defining one or more zones with each image having identical image-to-image zone locations, sizes, and shapes;
    for each image, computing an average pixel intensity for each zone to form a sequence thereof for each zone;
    for each zone, modifying the average pixel intensities by:
        computing the mean value of the sequence of average pixel intensities for such zone; and
        subtracting the mean from each average pixel intensity in the zone;
    for each zone sequence, computing a figure-of-merit;
    selecting the zone having the highest figure-of-merit; and
    using the sequence of pixel intensities of the selected zone to determine respiratory phase.

2. The method of determining respiratory phase of claim 1 wherein the figure-of-merit for a zone is based on estimates of power spectral density of the sequence of modified average pixel intensities for the zone.

3. The method of determining respiratory phase of claim 2 wherein the power spectral density estimates are determined using a maximum entropy method.

4. The method of determining respiratory phase of claim 3 wherein the figure-of-merit is the ratio of power in a predetermined frequency band to the power outside of the predetermined band.

5. The method of determining respiratory phase of claim 4 wherein the predetermined frequency band is defined by a low frequency $f_1$ and a high frequency $f_2$.

6. The method of determining respiratory phase of claim 5 wherein $f_1$ is 0.16 Hz and $f_2$ is 0.33 Hz.

7. The method of determining respiratory phase of claim 5 wherein the predetermined frequency band is centered around a prior estimate of respiratory rate.

8. The method of determining respiratory phase of claim 6 wherein the prior estimate of respiratory rate is provided by an external signal.

9. The method of determining respiratory phase of claim 2 wherein the power spectral density estimates are determined using a Fourier transform method.

* * * * *